(12) United States Patent
Oberreit et al.

(10) Patent No.: US 9,207,207 B2
(45) Date of Patent: Dec. 8, 2015

(54) DRIFT TUBE ION MOBILITY SPECTROMETER FOR AEROSOL MEASUREMENT

(71) Applicant: REGENTS OF THE UNIVERSITY OF MINNESOTA, Minneapolis, MN (US)

(72) Inventors: Derek Robert Oberreit, Roseville, MN (US); Christopher Joseph Hogan, Jr., Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/401,676

(22) PCT Filed: May 14, 2013

(86) PCT No.: PCT/US2013/040926
§ 371 (c)(1),
(2) Date: Nov. 17, 2014

(87) PCT Pub. No.: WO2013/173320
PCT Pub. Date: Nov. 21, 2013

(65) Prior Publication Data
US 2015/0115147 A1 Apr. 30, 2015

Related U.S. Application Data

(60) Provisional application No. 61/648,128, filed on May 17, 2012, provisional application No. 61/787,058, filed on Mar. 15, 2013.

(51) Int. Cl.
*H01J 49/26* (2006.01)
*H01J 49/00* (2006.01)
(Continued)

(52) U.S. Cl.
CPC .......... *G01N 27/622* (2013.01); *G01N 33/0027* (2013.01); *H01J 49/06* (2013.01); *H01J 49/22* (2013.01)

(58) Field of Classification Search
CPC .... G01N 27/622; G01N 27/624; H01J 49/004
USPC .......... 250/288, 281, 282, 283, 290, 292, 287
See application file for complete search history.

(56) References Cited

U.S. PATENT DOCUMENTS 6,797,943 B2   9/2004   Losch et al.
6,831,273 B2   12/2004  Jenkins et al.
(Continued)

FOREIGN PATENT DOCUMENTS

RU   2 328 791 C2   7/2008
RU   2 431 212 C1   10/2011
(Continued)

OTHER PUBLICATIONS

Bahadur et al., "Water uptake coefficients and deliquescence of NaCl nanoparticles at atmospheric relative humidities from molecular dynamics simulations," *Journal of Chemical Physics*, Sep. 7, 2008; 129(9):094508.
(Continued)

*Primary Examiner* — David A Vanore
(74) *Attorney, Agent, or Firm* — Mueting, Raasch & Gebhardt, P.A.

(57) ABSTRACT

A drift tube ion mobility spectrometry sample introduction scheme allows introduction of a sample packet at ground voltages. The sample packet of ionized particles is captured by subjecting particles within a defined region to an electric field at an elevated voltage. The ionized particles in the captured packet then migrate through the drift tube down the voltage gradient according to their electrical mobility. The particles are directed to a high sensitivity detector, such as a condensation particle counter (CPC), for detection.

22 Claims, 20 Drawing Sheets

(51) Int. Cl.
  *B01D 59/44* (2006.01)
  *G01N 27/62* (2006.01)
  *G01N 33/00* (2006.01)
  *H01J 49/06* (2006.01)
  *H01J 49/22* (2006.01)

(56) References Cited

U.S. PATENT DOCUMENTS

| | | | |
|---|---|---|---|
| 7,576,319 | B2 | 8/2009 | Miller et al. |
| 7,714,282 | B2 | 5/2010 | Guevremont et al. |
| 8,173,959 | B1 * | 5/2012 | Boumsellek et al. ......... 250/288 |
| 2005/0109931 | A1 * | 5/2005 | Schultz et al. ................ 250/287 |
| 2006/0284077 | A1 | 12/2006 | Fissan et al. |
| 2008/0173809 | A1 * | 7/2008 | Wu .............................. 250/283 |
| 2011/0057096 | A1 | 3/2011 | Fernandez de la Mora et al. |

FOREIGN PATENT DOCUMENTS

| | | |
|---|---|---|
| RU | 2010 120 961 A | 11/2011 |
| WO | 99/41585 | 8/1999 |
| WO | 2005/039780 A2 | 5/2005 |
| WO | 2012/027665 A1 | 3/2012 |

OTHER PUBLICATIONS

Biskos et al., "Nanosize effect on the deliquescence and the efflorescence of sodium chloride particles," *Aerosol Science and Technology*, Feb. 2006; 40(2):97-106.

Bruzewicz et al., "Reversible uptake of water on NaCl nanoparticles at relative humidity below deliquescence point observed by noncontact environmental atomic force microscopy," *Journal of Chemical Physics*, Jan. 28, 2011; 134(4): 044702.

Chen et al., "Electrospraying of Conducting Liquids for Monodisperse Aerosol Generation in the 4 Nm to 1.8 Mu-M Diameter Range," *Journal of Aerosol Science*, Sep. 1995; 26(6):963-977.

Chen et al., "Design and evaluation of a nanometer aerosol differential mobility analyzer (Nano-DMA)," *Journal of Aerosol Science*, Jun./Jul. 1998; 29(5/6):497-509.

Chen et al., "A High Efficiency, High Throughput Unipolar Aerosol Charger for Nanoparticles," *Journal of Nanoparticle Research*, 1999; 1:115-126.

Cheng et al., "Theory of a Screen-Type Diffusion Battery," *Journal of Aerosol Science*, 1980; 11:313.

Eiceman et al., *Ion mobility spectrometry*, 2nd ed. Boca Raton: CRC Press, 2005; Cover Page; Table of Contents; 11 pgs.

Ermak et al., "Numerical-Integration of the Langevin Equation—Monte-Carlo Simulation," *Journal of Computational Physics*, 1980; 35:169-182.

Grassian, et al., "Physicochemical properties of nitrate aerosols: Implications for the atmosphere," *Journal of Physical Chemistry A*, Oct. 26, 2006; 110:11785-11799.

Hinds, *Aerosol technology: properties, behavior, and measurement of airborne particles*, 2nd ed. New York: Wiley, 1999; Cover Page; Copyright Page; Table of Contents; 8 pgs.

Iida et al., "Effect of Working Fluid on Sub-2 nm Particle Detection with a Laminar Flow Ultrafine Condensation Particle Counter," *Aerosol Science and Technology*, 2009; 43:81-96.

International Search Report and Written Opinion for International Application No. PCT/US2013/040926, mailed Sep. 12, 2013; 8 pages.

International Preliminary Report on Patentability for International Application No. PCT/US2013/040926, mailed Nov. 18, 2014; 6 pages.

Jiang et al., "Transfer Functions and Penetrations of Five Differential Mobility Analyzers for Sub-2 nm Particle Classification," *Aerosol Science and Technology*, 2011; 45:480-492.

Kaufman, "Analysis of biomolecules using electrospray and nanoparticle methods: The gas-phase electrophoretic mobility molecular analyzer (GEMMA)," *Journal of Aerosol Science*, Jun.-Jul. 1998; 29(5/6):537-552.

Knutson et al., "Aerosol classification by electric mobility: apparatus, theory, and applications," *Journal of Aerosol Science*, 1975; 6:443-451.

Maitβer et al., "Determination of gas phase protein ion densities via ion mobility analysis with charge reduction," *Physical Chemistry Chemical Physics*, 2011; 13(48):21630-21641.

McGraw et al., "Deliquescence and efflorescence of small particles," *Journal of Chemical Physics*, Nov. 21, 2009; 131(19):194705.

Orr et al., "Aerosol size and relative humidity," *Journal of Colloid Science*, Oct. 1958; 13(5):472-482.

Park et al., "A study on effects of size and structure on hygroscopicity of nanoparticles using a tandem differential mobility analyzer and TEM," *Journal of Nanoparticle Research*, Jan. 2009; 11:175-183.

Puton et al., "Modelling of penetration of ions through a shutter grid in ion mobility spectrometers," *Sensors and Actuators B-Chemical*, Dec. 10, 2008; 135:116-121.

Rader et al., "Application of the Tandem Differential Mobility Analyzer to Studies of Droplet Growth or Evaporation," *Journal of Aerosol Science*, Oct. 1986; 17(5):771-787.

Ramiro et al., "Experimental validation of a high resolution nano-DMA," *Journal of Aerosol Science, Abstracts of the European Aerosol Conference* 2004; 35: S749-758.

Revercomb et al., "Theory of Plasma Chromatography Gaseous Electorphoresis—Review," *Analytical Chemistry*, Jun. 1975; 47:970-983.

Russell et al., "Deliquescence of small particles," *Journal of Chemical Physics*, Jan. 1, 2002; 116(1); 311-321.

Sakurai et al., "Hygroscopicity and volatility of 4-10 nm particles during summertime atmospheric nucleation events in urban Atlanta," *Journal of Geophysical Research-Atmospheres*, Nov. 27, 2005; 110; No. D22; 12 pgs.

Scheibel et al., "Generation of Monodisperse Ag-Aerosol and Nacl-Aerosol with Particle Diameters between 2-Nm and 300-Nm," *Journal of Aerosol Science*, 1983; 14(2):113.

Stolzenburg, "An Ultrafine Aerosol Size Distribution Measuring System," Thesis-Mechanical Engineering, University of Minnesota, Minneapolis, Jul. 1988; 14 pgs.

Tang, "Phase transformation and growth of aerosol particles composed of mixed salts," *Journal of Aerosol Science*, 1976; 7:361-371.

Tang et al., "An Investigation of Solute Nucleation in Levitated Solution Droplets," *Journal of Colloid and Interface Science*, Apr. 1984; 98(2):430-438.

Tang et al., "Water Activity Measurements with Single Suspended Droplets—the Nacl-H2o and Kcl-H2o Systems," *Journal of Colloid and Interface Science*, Dec. 1986; 114(2):409-415.

Tang et al., "Composition and Temperature-Dependence of the Deliquescence Properties of Hygroscopic Aerosols," *Atmospheric Environment Part A—General Topics*, Mar. 1993; 27A(4):467-473.

Ude et al., "Molecular monodisperse mobility and mass standards from electrosprays of tetra-alkyl ammonium halides," *Journal of Aerosol Science*, Oct. 2005; 36:1224-1237.

Vanhanen et al., "Particle Size Magnifier for Nano-CN Detection," *Aerosol Science and Technology*, 2011; 45:533-542.

Wang et al., "Fast mixing condensation nucleus counter: Application to rapid scanning differential mobility analyzer measurements," *Aerosol Science and Technology*, Jun. 2002; 36(6):678-689.

Wise et al., "Phase Transitions of Single Salt Particles Studied Using a Transmission Electron Microscope with an Environmental Cell," *Aerosol Science and Technology*, Sep. 1, 2005; 39(9):849-856.

Wyttenbach et al., "Design of a new electrospray ion mobility mass spectrometer," *International Journal of Mass Spectrometry*, Dec. 20, 2001; 212(1-3):13-23.

* cited by examiner

DRIFT TUBE ION MOBILITY SPECTROMETER FOR AEROSOL MEASUREMENT

RELATED APPLICATIONS

This application is a U.S. National Stage Application of International Application No. PCT/US2013/040926, filed on May 14, 2013, which claims the benefit of priority to U.S. Provisional Application No. 61/787,058 filed on Mar. 15, 2013 and U.S. Provisional Application No. 61/648,128 filed on May 17, 2012, all of which are incorporated herein by reference.

STATEMENT OF GOVERNMENT INTEREST

This invention was made with government support under CHE-1011810 awarded by the National Science Foundation. The government has certain rights in the invention

TECHNICAL FIELD

The present disclosure relates generally to ion mobility spectrometry and particularly to drift tube ion mobility spectral analysis of samples containing ionized species prior to analysis.

BACKGROUND

Ion mobility spectrometers (IMSs) are used to measure the electrical mobility of charged molecules or particles. Currently two main types of IMS devices exist: crossflow-type and drift tube-type.

Crossflow-type IMSs are commonly used in aerosol science, the most common of which are differential mobility analyzers (DMAs). In DMAs, ions or charged particles are introduced into a stream of gas between two parallel plates or concentric cylinders, across which a voltage differential is applied. The ions or charged particles are introduced through an inlet opening at one of the plates and migrate to the opposing plate following different trajectories according to their electrical mobility, which is a function of the drag coefficient. Particles within a given mobility range exit the DMA via a slit in the opposing plate. The voltage differential, carrier gas flow, exit slit size and location, etc. may be varied to select the electrical mobility range of particles that exit the DMA. The particles exiting the DMA may be directed to an ion detector or other instrument for further analysis.

The inlet plate or cylinder of a DMA is typically grounded, while the opposing plate or cylinder is typically at a negative or positive voltage. Thus, charged particles may readily enter the inlet of a DMA because there is no voltage potential to overcome. Accordingly, samples containing ionized species such as ambient environmental aerosols may be readily introduced into DMAs.

DMAs, however, have some drawbacks. First, the carrier gas flow rate tends to be quite high in order to effectively separate smaller charged particles, such as particles within the 1-10 nm range. In addition, DMAs tend to have a low resolving power for such smaller particles.

Drift tube-type IMSs (DT-IMSs) do not tend to suffer from the drawbacks of DMAs, which include low resolving power for small particles, high gas flow rates, and long measurement times. However, DT-IMSs present obstacles for aerosol measurements or sampling of particles that are charged prior to entering the DT-IMS. This feature is important for sampling aerosols where the user does not wish to alter the charge distribution or in cases where a charged aerosol has been selected by an upstream tandem device. Another obstacle of DT-IMSs for aerosol measurements is that DT-IMSs typically employ ion detectors having a low sensitivity. Ambient aerosols have ion concentrations that are often several orders of magnitude lower than molecular ion concentrations traditionally measured with DT-IMSs.

As indicated above, DT-IMSs are typically used for measurement of molecules or particles that are not initially charged. The uncharged molecules or particles enter a chamber across which an elevated voltage is applied. As the molecules are uncharged, their entry into the chamber is not significantly impeded by the voltage difference. However, particles that are charged or ionized prior to entering the chamber cannot readily cross the voltage barrier and thus cannot readily enter the chamber for analysis. Sampling of charged particles by a common DTIMS is possible through the use of a dielectric sampling port although the losses of charged particles would likely be high.

A schematic diagram that illustrates a generic DT-IMS 10 is shown in FIG. 1, with the voltage differential across the device shown. The molecules or particles to be analyzed are introduced through inlet 120 to enter a chamber 105 or portion of the drift tube 200 held at an elevated voltage. While in the chamber 105, an ionization source 165 is employed to ionize the particles. Once ionized the particles migrate in the drift tube 200 down the voltage differential, which is applied by a plurality of axially aligned conductive drift rings (not shown). An electronic gate 100 is typically employed to precipitate the particles until the gate is opened. The gate 100 is opened and then closed allowing a packet of particles to enter the drift zone 202, in which particles migrate towards a detector 150 down the voltage differential. A carrier gas is introduced through inlet 140 parallel to, but in opposing direction of, the direction of particle migration to purge the measurement region of unionized species. Particles reaching the ion detector 150 at various times after the opening of the gate 100 are detected, and data regarding the electrical mobility of the particle (which is proportional to the drift time) may be collected or analyzed. As shown in FIG. 1, the device 10 may include an outlet 130 for the carrier gas and may include an aperture grid 110 upstream of the detector 150. Most commonly, the detector 150 of a DT-IMS 10 is a Faraday plate, which tends to be insufficiently sensitive for the detection of ions or charged particles in concentrations typically found in aerosols.

SUMMARY

Various embodiments of methods, devices and systems that provide for ambient sampling of aerosols containing ionized particles in a DT-IMS are described herein. A sample introduction scheme that allows introduction of a sample packet at ground voltages is described. The sample packet of ionized particles is captured by subjecting particles within a defined region to an electric field at an elevated voltage. The ionized particles in the captured packet then migrate through the drift tube down a voltage gradient at a velocity dependent upon their electrical mobility. In embodiments, the particles are directed to a high sensitivity detector, such as a condensation particle counter (CPC) for detection. CPCs may have sensitivities in the range desired for detecting particles in concentrations typically present in ambient environmental samples. Embodiments of the devices, methods and systems described herein allow for fast, high resolution measurement of aerosol distributions in the 2-30 nm size range, which is desirable for, among other things, environmental monitoring, process control, and high throughput screening.

In embodiments described herein, a method includes (i) introducing a sample aerosol into a drift tube of an ion mobility spectrometer, and (ii) introducing a carrier gas into the drift tube such that at least a portion of the carrier gas flows through the drift tube in a direction generally opposing migration of ionized particles through the drift tube. The sample aerosol and carrier gas are introduced into the drift tube such that the sample aerosol circulates within the drift tube in a manner such that (i) a portion of the sample aerosol circulation is within a region of the drift tube to which an electrostatic field is capable of being applied for purposes of ion mobility separation and (ii) a portion of the sample aerosol circulation is in a portion of the drift tube in which the electrostatic field, when applied, effectively blocks migration of additional ions into the separation region. The method further comprises applying an electric field to the drift tube for purposes of ion mobility separation, wherein the application of the electric field increases the electrical potential of ionized particles within the sample circulation in the region of the drift tube to which the electrostatic field is applied. The ionized particles to which the electric field for the purposes of ion mobility separation is applied migrate in the tube down a gradient of the applied field against the flow of the carrier gas to separate according to their ion mobility.

In embodiments described herein, a method comprises (i) introducing a sample aerosol into a drift tube of an ion mobility spectrometer; and (ii) introducing a carrier gas into the drift tube of the ion mobility spectrometer such that at least a portion of the carrier gas flows through the drift tube in a direction generally opposing migration of ionized particles through the drift tube. The sample aerosol and carrier gas are introduced into the drift tube such that the sample aerosol circulates within a portion of the drift tube. An applied electrostatic separation field blocks migration of ionized particles in the sample aerosol into a separation region of the drift tube. The method further includes applying a capturing electric field to the drift tube to increase the electrical potential of ionized particles within at least a portion of the sample circulation to a potential greater than that of the applied electrostatic separation field to allow the ionized particles at the increased potential to migrate in the drift tube down a gradient of the applied separation field against the flow of the carrier gas to separate according to their ion mobility.

DT-IMSs and systems including DT-IMSs that are configured to carry out or assist in carrying out such a method are also described herein.

In embodiments, a DT-IMS operably coupled to a condensation particle counter (CPC) is described. The DT-IMS may be configured such that carrier gas used to oppose the migration of charged particles down an electrical gradient for purposes of ion mobility separation is also used to carry separated ionized particles to an inlet of the CPC.

One or more embodiments of the systems, devices, and methods described herein provide one or more advantages over prior DT-IMS devices, systems and methods, such as the ability to sample pre-charged particles, the ability to detect particles in low concentration, and the like. Another advantage that may be realized by one or more embodiments described herein is the ability to measure vapor uptake by aerosol particles introduced into the DT-IMS. Such measurements are made possible because of the improved resolving power of DT-IMSs relative to DMAs for small (<10 nm) particle diameters and because of the relatively low gas flow rates of DT-IMSs relative to DMAs, which were previously employed for aerosol analysis. The high gas flow rates required by high resolution DMAs which aspirate aerosol samples would require such high volumes of vaporized liquid, such as water, that altering the vapor concentration would not be practicable. However, with significantly lower carrier gas flow rates, DT-IMS as described herein may be employed to test the uptake of vapor by ionized particles. Additionally, high resolution DMAs that are currently available suffer from poor transmission efficiency. One of skill in the art will understand these and other advantages upon reading the present disclosure.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

Any direction referred to herein, such as "top," "bottom," "left," "right," "upper," "lower," "above," "below," and other directions and orientations are described herein for clarity in reference to the figures and are not to be limiting of an actual device or system or use of the device or system. Many of the devices, articles or systems described herein may be used in a number of directions and orientations.

The present disclosure describes, among other things, methods, devices and systems that provide for sampling of aerosols containing ionized particles in a DT-IMS. Schemes that allow introduction of pre-charged particles into a DT-IMS are described in more detail below. Schemes that channel separated particles to a particle counter are also described in more detail below.

Figure 1:
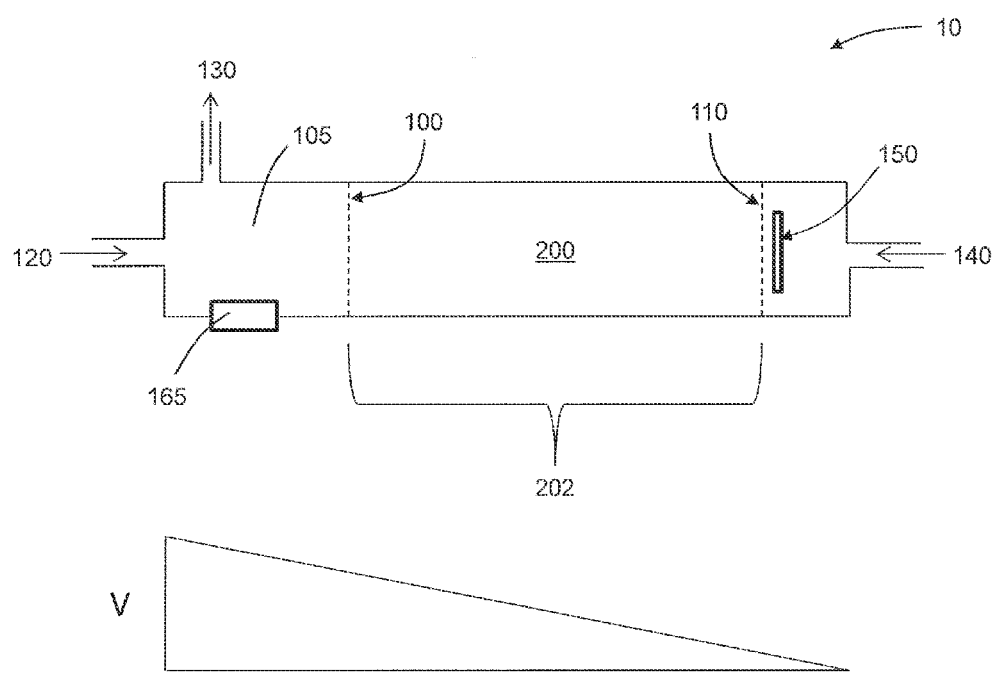
FIG. 1 is a schematic drawing of an example of a generic drift tube-type ion mobility spectrometer (DT-IMS) and associated voltage across the length of the device.
Figure 2:
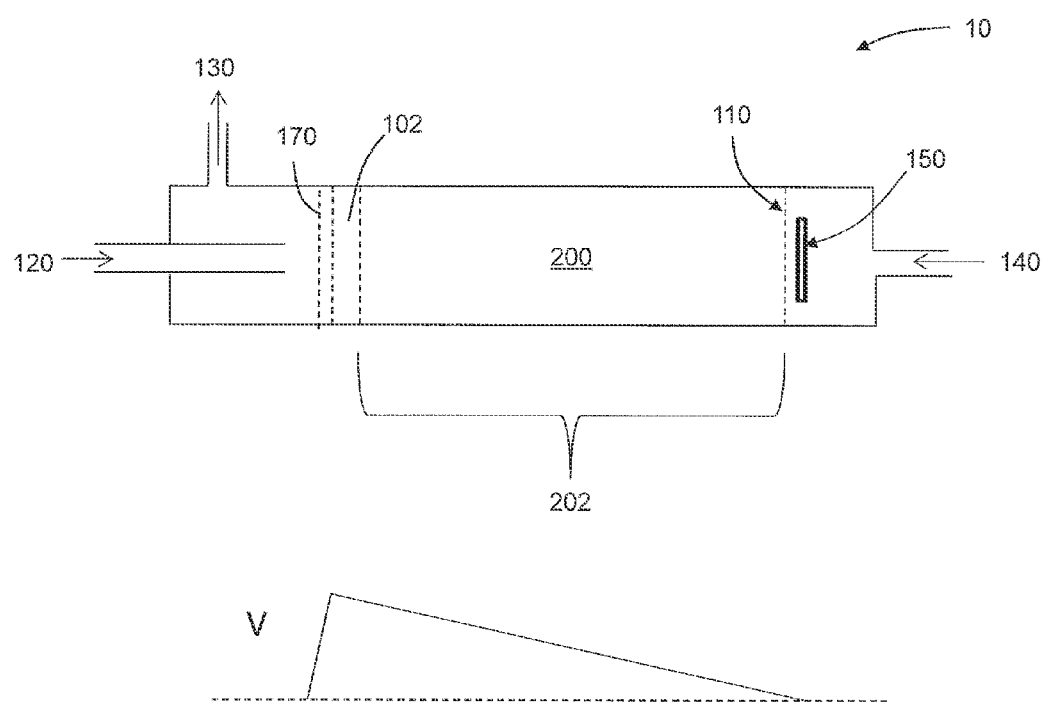
FIGS. 2-4 are schematic diagrams illustrating DT-IMSs and associated voltages in accordance with embodiments described herein.

Referring now to FIG. 2, an embodiment of a DT-IMS 10 is shown along with an example of voltage along the length of the drift tube 200, which is applied via a plurality of axially aligned conductive drift rings (not shown). The voltage is shown below the schematic of the device. Initially, the voltage across the device may be at ground. A voltage scheme as depicted in FIG. 2 may then be applied to capture a sample packet present with a capture zone 102, driving ionized particles within the packet to a higher electrical potential. A gradient-defining screen 170, such as a wire mesh or the like, may optionally be disposed at or near the voltage peak location to more sharply defined the profile. While not depicted or described with regard to some other embodiments described herein, it will be understood that a gradient-defining screen may optionally be used with these other embodiments.

It will also be understood that the applied voltage shown in FIG. 2, or other figures presented herein, may be of positive or negative polarity. The depicted voltage may be considered to represent the absolute value of the voltage. The dashed line depicted in the voltage scheme represents ground. While shown as linear, it will be understood that the voltage profile may be non-linear. The magnitude of the applied voltage may also change throughout the measurement time.

Once the voltage scheme is applied, ionized particles migrate within the drift tube 200 down the voltage potential to an ion detector 150, which may be a Faraday plate, positioned in the drift tube. As described in more detail below other detection schemes may be employed, including schemes where the detector is located outside of the drift tube. An aperture grid 110 or screen may be present upstream (relative to flow of ionized particles) of the detector 150.

The captured ionized particles separate within the drift zone 202 according to their electrical mobility against a stream of carrier gas introduced at inlet 140. The carrier gas may exit the device 10 at outlet 130. The flow of carrier gas through the inlet 140 and outlet 130 may be controlled to achieve desired flow characteristics, such as laminar flow, within the drift zone 202.

Aerosol samples are introduced through inlet 120 in a circulating pattern near a point in the device where the electrostatic field, in the direction of the axis of the drift tube 200, is at zero (even when the voltage is applied, as will be described in more detail below with regard to FIG. 5). While only one inlet is shown, it will be understood that in the various embodiments described herein, more than one inlet may be present and may be used to achieve desired flow and circulation. The flow of the carrier gas that is introduced at inlet 140 helps define the circulatory pattern of the sample. At the start of analysis the voltage is applied to the electrodes (e.g. drift rings—not shown) and only aerosol particles that are downstream (relative to flow of ionized particles in drift tube when voltage applied—i.e., from direction of inlet 120 to detector 150) of the zero electrostatic potential gradient region are captured and subjected to IMS separation through the drift zone 202. Once the voltage is applied, charged species in the sample will not enter the capture zone 102 due to the voltage barrier. The voltage may be returned to ground, and voltage scheme reapplied to capture another sample packet.

Sample introduction shown in FIG. 2 is "gateless." Such a gateless introduction is possible because the capture zone 102 can be well defined by controlling flows of the carrier gas and the sample aerosol. Thus, the captured sample packet that is subjected to separation according to electrical mobility is geometrically restricted and may not, in some cases, significantly adversely affect resolving power.

Figure 3:
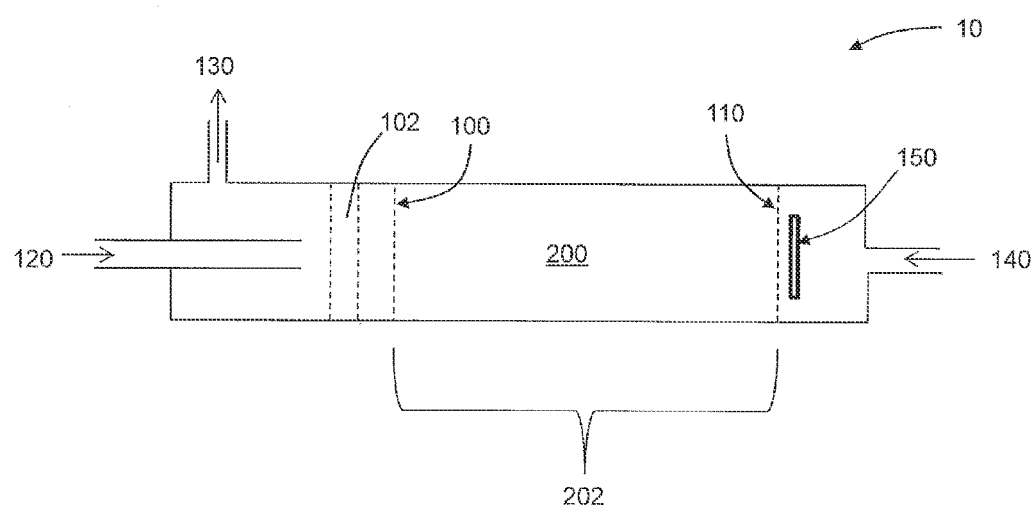
Figure 3:
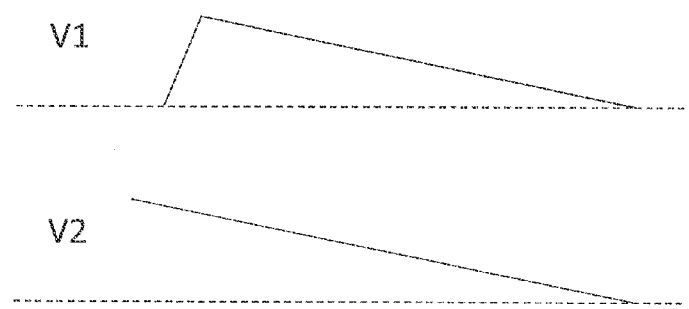

Of course, it is possible to employ a gate in a DT-IMS as described herein. For example and with reference to FIG. 3 an example of a DT-IMS 10 that includes a gate 100 is shown. The device 10 in FIG. 3 is similar to the device shown in FIG. 2, with like numbers referring to like components, regions, or the like. As with the device in FIG. 2, the device 10 in FIG. 3 is configured to allow sample introduction into capture zone 102 at zero voltage. A loading voltage V2 is then applied (e.g., as depicted below the device schematic) to increase the electrical potential of charged particles within capture zone 102, which migrate down the drift tube 200 until they reach the electronic gate 100. The gate 100 may be opened to allow a packet of ionized sample particles to enter the drift zone 202 and then closed. Once in the drift zone 202, particles migrate in the drift tube against the flow of carrier gas down the voltage potential (V1). Timing of particle detection at detector 150 may then be correlated to timing of opening of gate 100, as is currently done with most DT-IMS devices. An advantage of this configuration is that the drift field does not abruptly change at the start of a sample which may cause adverse effects on certain detectors 150, such as Faraday plate electrometers. Of course, the use of separate capture and separation voltages may be employed with or without an electronic gate.

Figure 4:
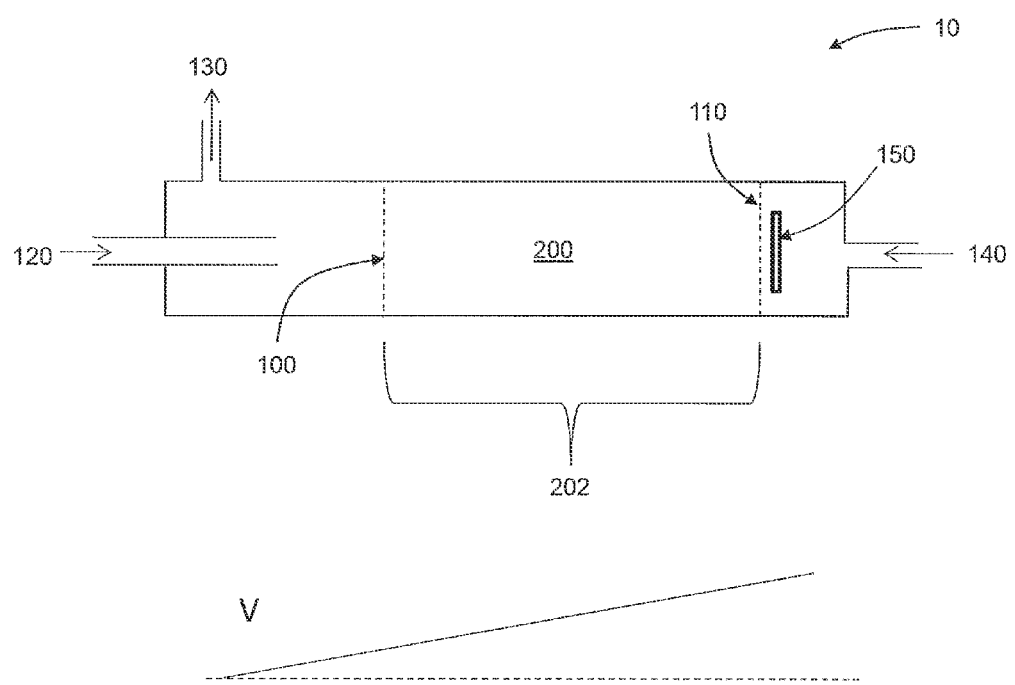

Referring now to FIG. 4, a reverse field (e.g. ground at the inlet 120 and higher voltage at the detector 150) may also be used to introduce charged samples into the drift zone 202. In such cases, an electronic gate 100, such as described above, may be desirable to introduce packets of sample. In the embodiment depicted in FIG. 4, the gate 100 may be placed in proximity to the inlet 120. In this case, the capture zone (not shown in FIG. 4), which is located upstream of the gate, is not as dependent on the flow pattern of analyte into the tube 200. Any aerosol that (i) enters through the inlet 120; (ii) is captured by the electric field (which may extend to the inlet 120); and (iii) passes the gate 100 may serve as analyte.

In embodiments such as those depicted in FIG. 4, a detector 150 that is not significantly adversely affected by such voltages is preferably employed. One of skill in the art will understand that Faraday plate detectors and condensation particle counters (CPCs) can, in theory, be operated at high voltage.

While not shown, it will be understood that a DT-IMS as described herein may include an ionization source to ionize sample particles within drift tube. While the aerosol sample entering the drift tube may already contain charged particles, it may be desirable to further ionize the particles to obtain a sample with standardized particle ion distribution. The ionization source may be positioned in or upstream (relative to ion drift) of the capture zone. Of course, the ionization may also take place upstream of inlet.

Figure 5:
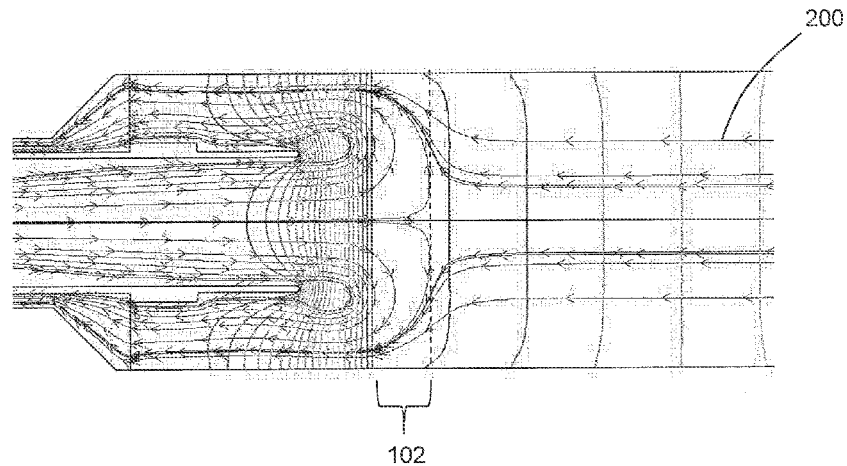
FIG. 5 is a schematic image of a simulation of sample flow pathlines and iso-potential lines in a portion of a DT-IMS in which charged particles of the sample may be captured. The isopotential lines range from 0V (blue) to the operating drift voltage (red).

Referring now to FIG. 5, simulated sample flow path lines and electrostatic potential contours in a portion of a drift tube 200 around the capture zone 102 is shown. As depicted, the drift tube 200 includes a plurality of axially aligned drift tube rings separated by spacers. When a voltage is applied to the rings, electrostatic potential contours as shown may result. In the depicted drawing, the electrostatic potential contours range from 0V up to the applied operating voltage. Only aerosol sample ion particles that are to the right of the zero gradient region (generally those particles within the capture zone 102) will be subjected to ion mobility separation in the drift tube 200.

Figure 6:
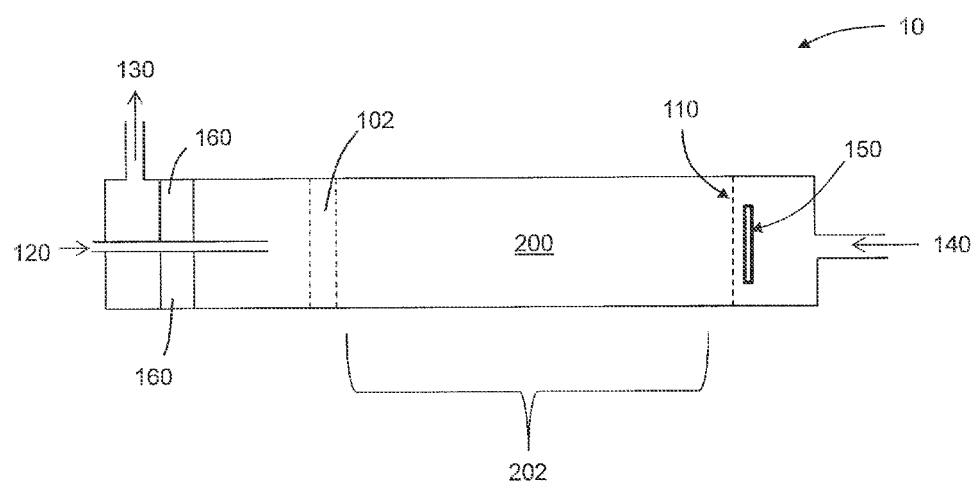
FIG. 6 is a schematic diagram illustrating an embodiment of a DT-IMS.

Referring now to FIG. 6, in which a device 10 similar to the device in FIG. 2 is shown, the device 10 may include a diffuser 160 to assist in achieving the desired circulation pattern of the sample that is introduced through inlet 120. The geometry and position of the diffuser 160, the geometry of the drift tube 200, the rate of flow of the sample, and the rate of flow of the carrier gas may all affect the circulation pattern of the sample flow, and each may be readily varied by those of skill in the art to obtain a sample flow pattern with a defined capture zone 102 at an appropriate point relative to an electric field, when applied (such as depicted in FIG. 5).

Figure 7:
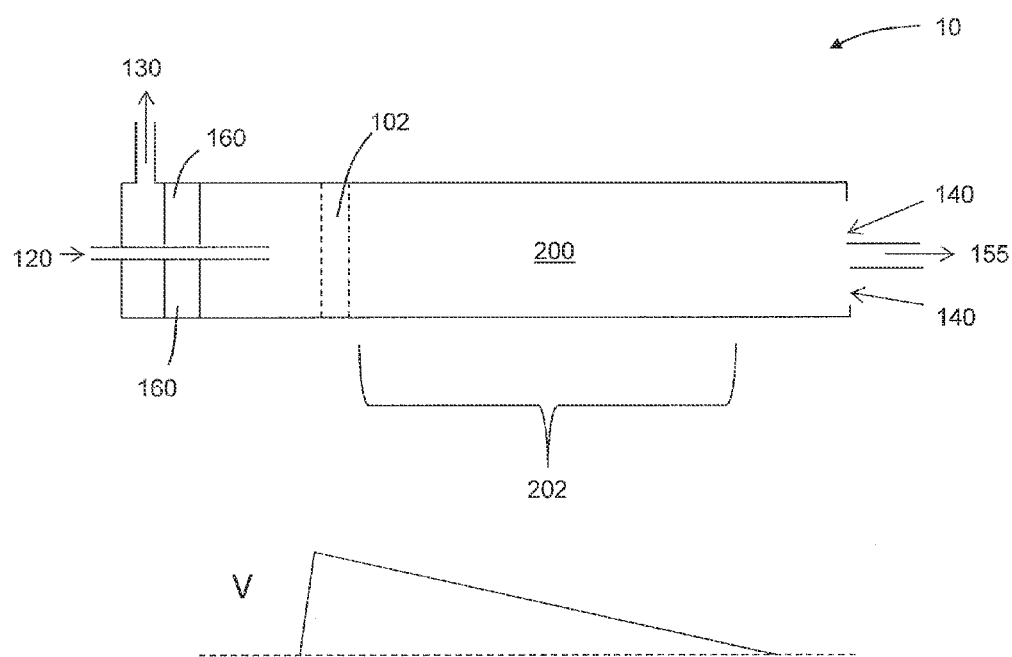
FIG. 7 is a schematic diagram illustrating a DT-IMS and associated voltage in accordance with embodiments described herein.

Referring now to FIG. 7, a DT-IMS device 10 in which a detector is located external to the drift tube 200 is shown. In the depicted embodiment, ionized particles that separate as they migrate towards the end of the drift tube 200 are carried by a stream of carrier gas through a conduit 155. In embodiments, the carrier gas that carries the separated ion particles through the conduit 155 to the detector is also the carrier gas that serves as the drift gas for the ion mobility separation. The carrier gas is introduced through inlet 140. The drift tube 200, conduit 155 and inlet 140 are configured, and the gas flow controlled, to achieve carrier gas flow that allows the carrier gas to serve as both the drift gas and the carrier gas through the conduit.

Figure 8:
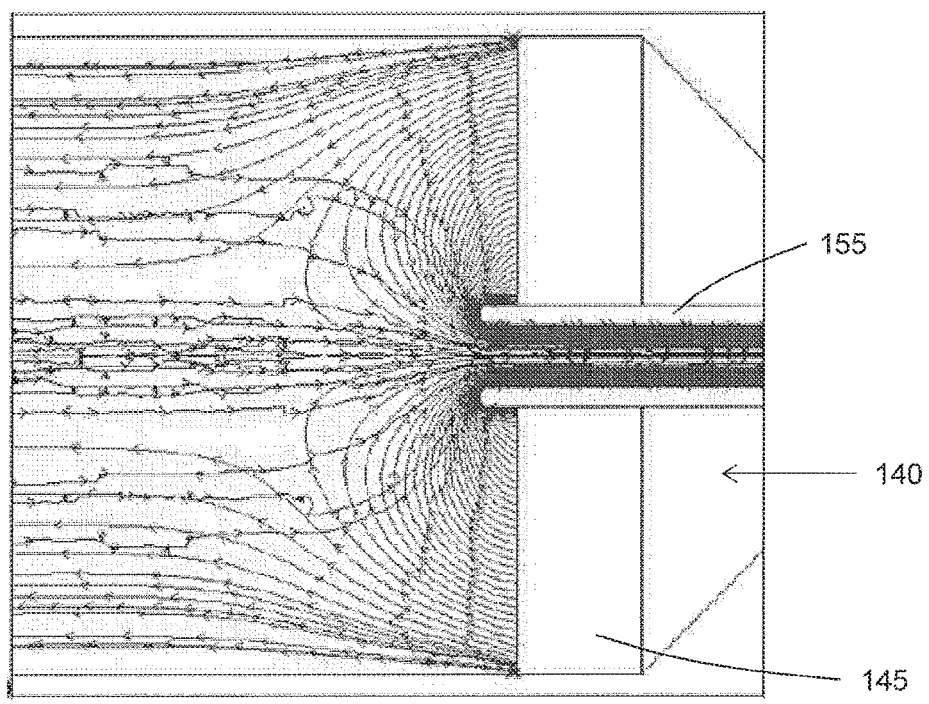
FIG. 8 is a schematic image of a flow path in a portion of a DT-IMS in which ionized particles are directed towards a detector. The particle path lines are shown in blue, and the carrier gas flow pathlines are shown in red.

By way of example and with reference to FIG. 8, a schematic image of a flow path lines in a portion of a DT-IMS in which ionized particles are directed towards a detector is shown. The sample flow path lines are shown generally in the center. Preferably, the sample flow is directed to conduit at a point at which the sample is no longer under the influence of voltage-driven migration. As shown, a flow diffuser 145 may be employed to facilitate desired flow paths. In embodiments, the carrier gas is introduced through the inlet 140 at a flow rate that equals the detector flow plus the drift gas flow.

In embodiments, particles are focused in the drift tube via application of a non-linear electric field along the length of the drift tube. Such focusing of particles may be advantageous when an external detector is used (e.g. as discussed above with regard to FIG. 7); e.g., where it is advantageous or desirable to focus particles to a limited region or area of the drift tube. It should be understood that such focusing of charged particles, particularly in aerosols, may be useful in applications other than just DT-IMS. For example, a drift tube may be used with, or without, counter flow of carrier gas to focus particles for further analysis in nearly any suitable system.

With regard to DT-IMS, particle trajectory simulations show that a significant portion of sampled aerosol may be deposited on the ground electrode (grounded diffuser) at the end of the drift region versus being drawn into the detector (when an external detector is employed). This effect is in some ways beneficial in that the particles that are ultimately sampled have experienced a more uniform drag force from the drift gas leading to better resolution. For low number concentration aerosols where resolution is not as critical, the aerosol can be focused by exploiting the Poisson-Laplace equation in the absence of spatial charge, $$\nabla^2 V=0 \tag{1}$$

where V is the voltage potential. The Laplacian can be written in cylindrical coordinates, $$\frac{1}{r}\frac{\partial}{\partial r}\left(r\frac{\partial V}{\partial r}\right)+\frac{\partial^2 V}{\partial z^2}=0, \tag{2}$$

due to the axial symmetry of the drift tube geometry. The electric field in the device is determined by the voltage gradient $$\nabla V=-\vec{E}, \tag{3}$$

which allows Equation 2 to be written as $$\frac{1}{r}\frac{\partial}{\partial r}(-rE_r)+\frac{\partial}{\partial z}(-E_z)=0, \tag{4}$$

where $E_z$ and $E_r$ are the electric fields in the axial and radial directions. For typical applications of drift tubes, $E_z$ is constant and therefore $E_r$ must be zero. If $E_z$ varies with the axial position z then a radial field $E_r$ is present and can be exploited to guide charged particles towards, or away from, the axis. If the value for $$\frac{\partial}{\partial z}(-E_z) = \frac{\partial^2}{\partial z^2} V = f(z) \quad (5)$$

Equation 4 can then be written as $$\frac{1}{r}\frac{\partial}{\partial r}(rE_r) = f(z), \quad (6)$$

leading to $$d(rE_r) = f(z)rdr \quad (7)$$

Which after integration gives and removal of an integration constant (such that the field remains found at r=0):

$$E_r = \frac{f(z)r}{2} \quad (8)$$

Equation 8 shows that when the magnitude of $E_z$ is increasing along the axis then there is a corresponding gradient $E_r(r)$ that is acting radially in the opposite direction (pushing ions towards the center of the drift region).

Figure 9:
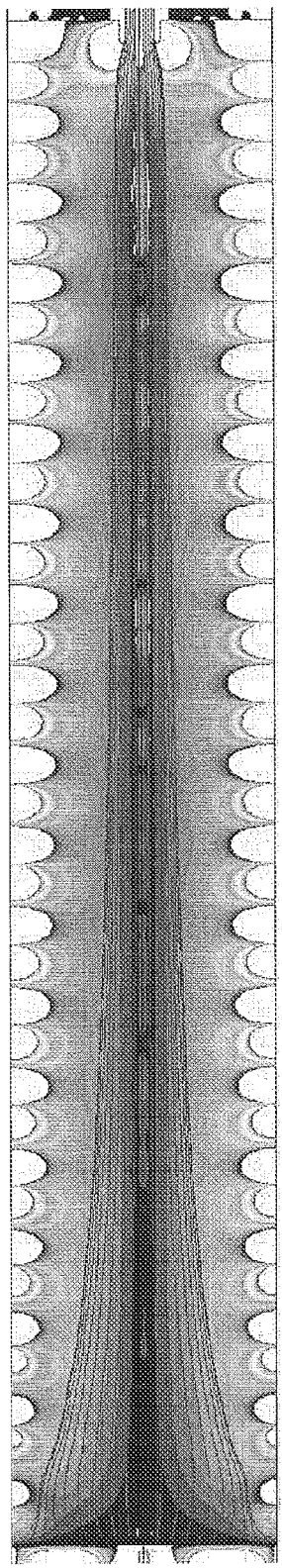
FIG. 9 is a schematic simulated image of particle pathline focusing achieved by a non-constant axial electrostatic field.

FIG. 9 shows pathlines for 2 nm particles along with the gradient $E_r$ (blue represents $E_r=0$, red is $E_r=1000$ V/m) for V(z) set at V=−19000 $z^2$−95 z+1000 which represents an example case for a prototype geometry with $r_{max}=0.002$ m, $r_{min}=0.002$ m, and $z_{end.}=0.227$ m.

In the embodiments discussed above, the drift voltage is described as being generally "on" or "off" instantaneously or nearly instantaneously. However, it will be understood that the voltage may be ramped, stepped, or otherwise changed from "off" to "on." Simulations have shown that, for a given drift voltage, ions with a high drift velocity relative to the drift gas velocity are not efficiently sampled. Conversely if the ion drift velocity is on the same order as the drift gas velocity the laminar flow profile can negatively impact overall resolution. In order to efficiently sample ions across a wide range of mobilities, the drift voltage may be ramped, stepped, or otherwise changed throughout the analysis, such that high mobility ions are sampled under a low field (low drift velocity) at the early part of the ramp and ions with lower mobility spend a significant portion of their measurement time at a suitably high drift velocity. Laboratory experiments, in the context of a test system described herein, have shown that ramping linearly from 500V to 9 kV over a span of 20 seconds provides a much more uniform sampling efficiency.

Figure 10:
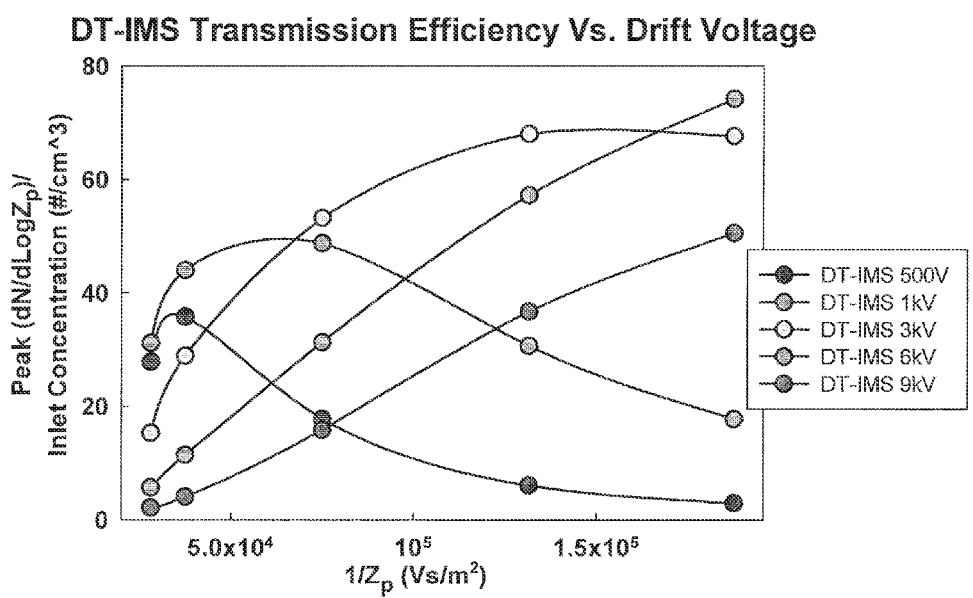
FIG. 10 is a plot of measured transmission efficiency as a function of electrical mobility for different drift voltages.

Transmission efficiency measurements of the DTIMS show a dependence on particle size and drift voltage as shown in FIG. 10.

The losses of small particles at high drift voltages are attributed to the increased drift velocity near the detector inlet causing a higher fraction of particles to precipitate at the end of the drift region opposed to being aspirated by the detector. The reduced transmission efficiency for large particles at low drift flows are likely due to the longer drift times and associated diffusion losses to the walls of the device. This effect can be reduced by ramping, stepping or otherwise changing the drift voltage from a low value to a higher value (linearly, non-linearly or by some other time dependence) throughout the measurement.

Figure 11:
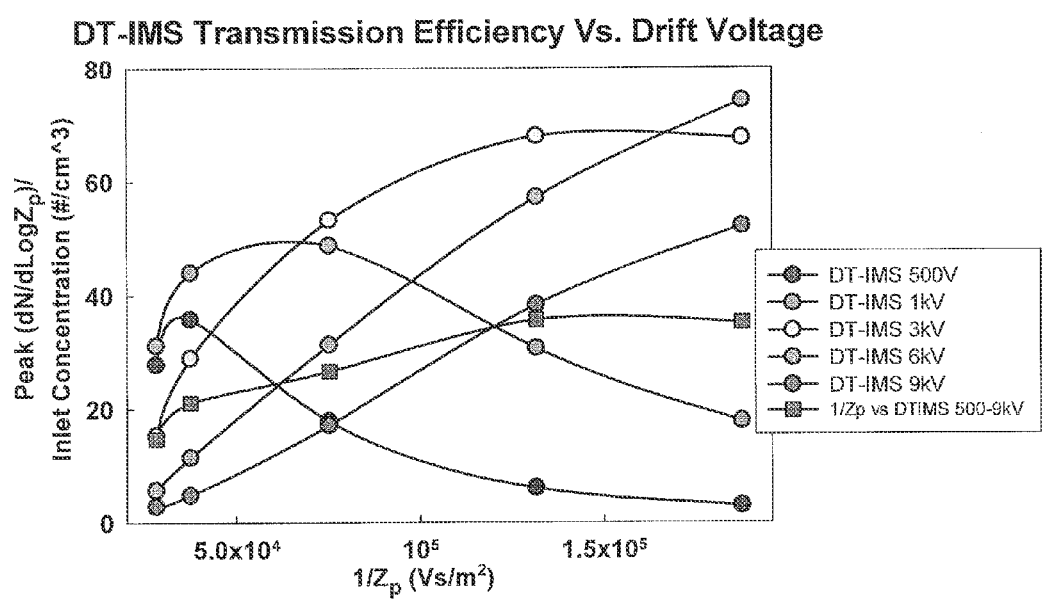
FIG. 11 is a plot of measured transmission efficiency as a function of electrical mobility including results including voltage ramping.

FIG. 11 shows the transmission efficiency for a voltage ramp beginning at 500V and rising linearly to 9 kV over 20 seconds.

As shown in FIG. 11, the transmission efficiency for small particles is improved by voltage ramping as is the uniformity of transmission efficiency vs. size. Further improvement should be achievable by those of skill in the art by manipulation of the ramping scheme.

The DT-IMS devices and methods described herein include DT-IMS with or without gating, with an applied electric field that is linear, non-linear, time invariant, time variant, with a voltage profile that is linear, non-linear, time invariant or time variant, or combinations thereof.

Figure 12:
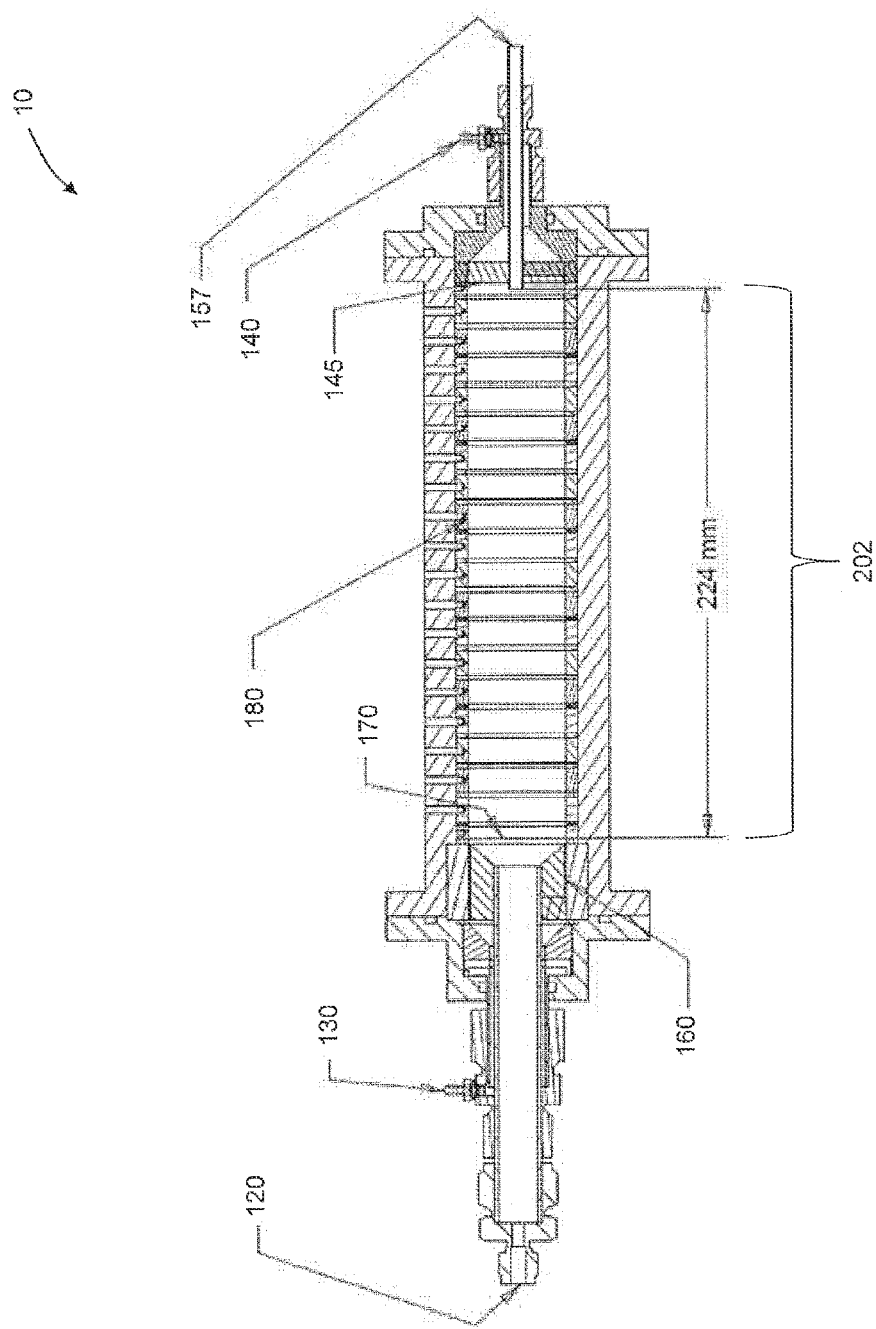
FIG. 12 is a schematic cross sectional view of an example an embodiment of a DT-IMS.

Referring now to FIG. 12, a schematic cross sectional diagram of an embodiment of a DT-IMS similar to the device depicted in FIG. 7 is shown. The device 10 may employ one or more principles discussed above; e.g.: flow rate and geometric control for sample packet capture; application of voltage to capture sample packet; application of voltage contours for focusing; ramping or stepping to increase transmission frequency; etc. The device depicted in FIG. 12 contains a sample inlet 120, flow outlet 130, an inlet diffuser 160, a screen 170, drift rings 180, an exit diffuser 145, a flow inlet 140, and a detector inlet 157. In the depicted embodiments, the drift zone 202 has a length of 224 mm Of course, the drift zone may have any suitable length or other dimension. A gradient-defining screen (such as screen 170 depicted in FIG. 12) may be included in any of the embodiments disclosed herein where suitable or desirable. The screen serves to provide a sharp electromagnetic edge to the "packet" introduced into the drift tube.

Figure 13:
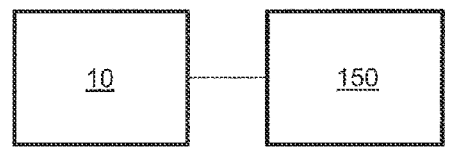
FIGS. 13-15 are schematic block diagrams of various systems that include a DT-IMS in accordance with embodiments described herein.
Figure 14:
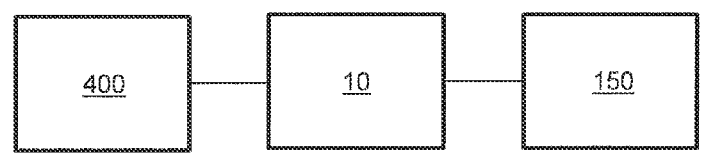
Figure 15:
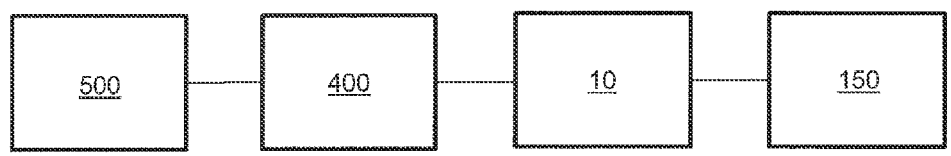

Referring now to FIGS. 13-15, block diagrams of various systems employing a DT-IMS 10 as described herein are shown. The DT-IMS 10 may be coupled to an ion or particle detector 150, which may be located within the drift tube or external to the drift tube. In embodiments, the detector 150 is a condensation particle counter (CPC), such as a TSI Model 3786 CPC or 3788 WCPC. CPCs typically have high ion detection sensitivity, often allowing counting of single particles.

Figure 16:
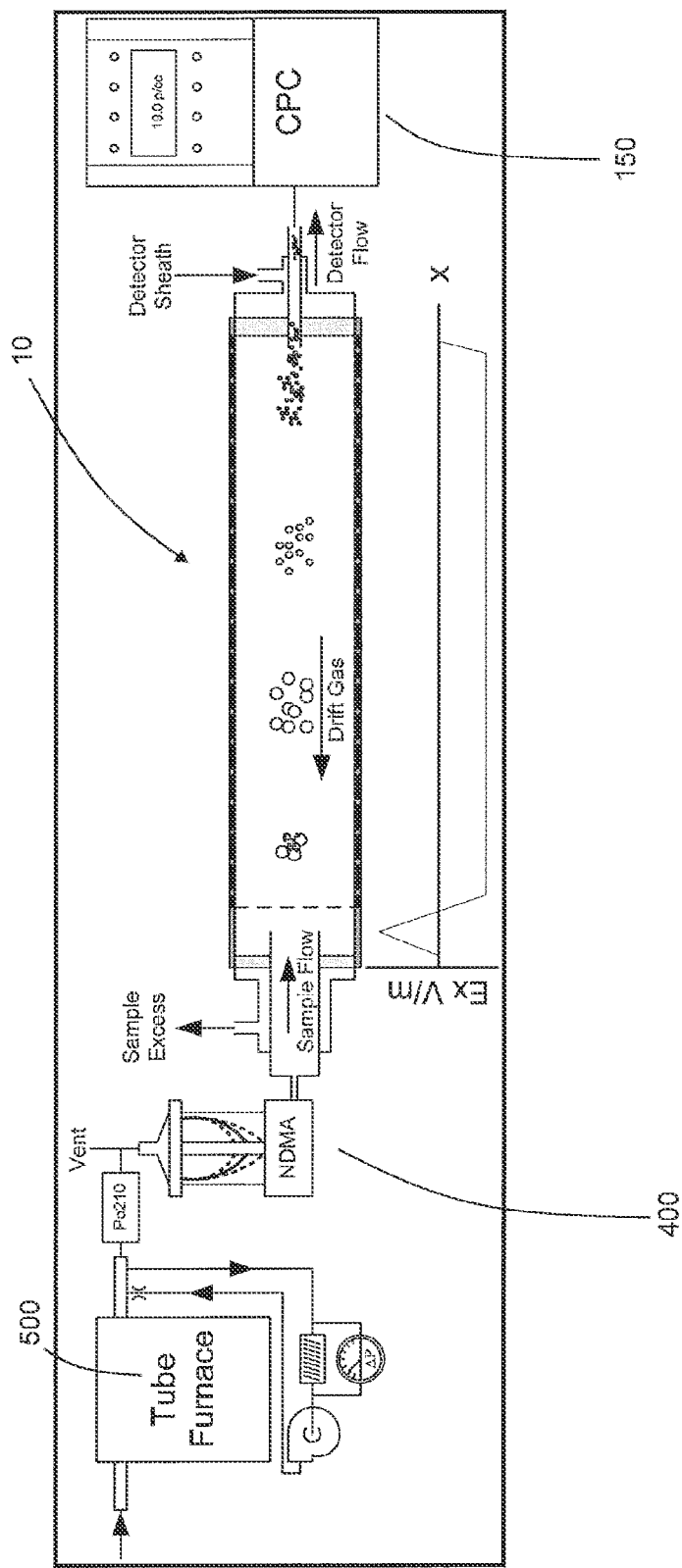
FIG. 16 is a schematic block diagram of a tandem nano-DMA (nDMA) DT-IMS-CPC system in accordance with embodiments described herein.

In embodiments, the DT-IMS may be placed in tandem with an upstream particle selector 400. In embodiments, the upstream particle selector 400 is a DMA device, such as nDMA device (e.g., TSI model 3085), which will feed particles of a preselected size range into DT-IMS for analysis of size shifts due to aerosol modification between the DMA and the DT-IMS. In embodiments, the particles are in the range from about 1 nanometer to about 100 nanometers, such as from about 2 nanometers to about 30 nanometers. The ions or charged particles exiting the DMA may be modified in size, charge state, morphology or chemical composition by an appropriate reaction cell prior to introduction to the drift tube inlet. Of course, the drift tube may serve as a reaction cell in which size, charge state, morphology or chemical composition, etc. may be modified, regardless of whether the system includes an upstream DMA.

An aerosol generation system such as an electrospray aerosol generator, furnace, or aerosol nebulizer 500 may be placed upstream of the DT-IMS 10 to produce sample aerosols for introduction to the DT-IMS 10 or upstream particle separator 400. However, when ambient aerosols are to be sampled, the use of an aerosol generation system 500 may be omitted.

Referring now to FIG. 16, a schematic block diagram of a tandem nano-DMA (nDMA) DT-IMS-CPC system in accordance with embodiments described herein. As depicted, the system includes a furnace 500 to generate aerosol particles, a nDMA 400, a DT-IMS 10 and a CPC 150. A system as depicted in FIG. 16, where the DT-IMS was generally as depicted in FIG. 12, was used in initial characterization as described herein below in the EXAMPLES.

While not shown, it will be understood that devices or systems as described herein include appropriate electronics configured to control, operate, integrate, etc. various aspects or functions of the device or system. The electronics may include a power supply, a processor, memory, circuitry or other components necessary or desirable for a device or system to carry out the methods or processes described herein.

A number of different aspects of methods, apparatuses and systems are described herein a summary of some selected aspects is presented below.

In a first aspect, a method includes introducing a sample aerosol into a drift tube of an ion mobility spectrometer and introducing a carrier gas into the drift tube of the ion mobility spectrometer such that at least a portion of the carrier gas flows through the drift tube in a direction generally opposing migration of ionized particles through the drift tube. The sample aerosol and carrier gas are introduced into the drift tube such that the sample aerosol circulates within a portion of the drift tube. An applied electrostatic separation field blocks migration of ionized particles in the sample aerosol into a separation region of the drift tube. The method further includes applying a capturing electric field to the drift tube to increase the electrical potential of ionized particles within at least a portion of the sample circulation to a potential greater than that of the applied electrostatic separation field to allow the ionized particles at the increased potential to migrate in the drift tube down a gradient of the applied separation field against the flow of the carrier gas to separate according to their ion mobility.

A second aspect is a method according to the first aspect, further comprising detecting the separated ionized particles via a particle detector and correlating the detection of the particles with the timing of the application of the capturing electric field.

A third aspect is a method according to the first aspect, further comprising deactivating an electronic gate to allow at least a portion of the ionized particles having the increased potential to pass through the gate, wherein the gate is positioned within the drift tube electrically downstream of the sample circulation region.

A fourth aspect is a method according to the third aspect, further comprising detecting the separated ionized particles via a particle detector and correlating the detection of the particles with the timing of the deactivation of the gate.

A fifth aspect is a method according to any one of aspects 1-4, further comprising carrying the separated ionized particles via a stream of the carrier gas to a particle detector external to the drift tube.

A sixth aspect is a method according to the fifth aspect, wherein the separated ionized particles are carried in a conduit, and wherein the drift tube, the conduit and flow of carrier gas is configured to cause a portion of the carrier gas to flow in the drift tube against the migration of the ionized particles down the gradient of the electric field and to cause a portion of the carrier gas to flow in the conduit A seventh aspect is a method according to any one of aspects 1-7, wherein the particle detector is a condensation particle counter.

An eighth aspect is a method according to any one of aspects 1-7, wherein applying the capturing electric field to the drift tube for purposes of ion mobility separation comprises applying the electric field such that a maximum voltage differential is achieved instantaneously or nearly instantaneously.

A ninth aspect is a method according to any of aspects 1-8, wherein the electrostatic separation field is ramped or stepped over time.

A tenth aspect is a method according to any one of aspects 1-9, wherein introducing the sample aerosol into the drift tube of the ion mobility spectrometer comprises obtaining precursor aerosol and modifying the precursor aerosol to form the sample aerosol.

An eleventh aspect is a method according to the tenth aspect, wherein obtaining the precursor aerosol comprises selecting aerosol particles having a predetermined range of ion mobility.

A twelfth aspect is a according to the eleventh aspect, wherein selecting the aerosol particles having the predetermined range of ion mobility comprises separating the particles via a differential mobility analyzer.

A thirteenth aspect is a method according to any one of aspects 10-12, wherein modifying the precursor aerosol comprises modifying the size, charge state, morphology or chemical composition of particles of the precursor aerosol to form the sample aerosol.

A fourteenth aspect is a method according to any one of aspects 1-13, wherein the carrier gas introduced into the drift tube comprises vaporized liquid.

A fifteenth aspect is a method according to any one of aspects 1-14, wherein the separation field is a non-constant field configured to focus particles towards the center of the drift tube as the particles migrate through the drift tube In a sixteenth aspect, a method comprises: (i) introducing a sample aerosol into a drift tube of an ion mobility spectrometer; and (ii) introducing a carrier gas into the drift tube of the ion mobility spectrometer such that at least a portion of the carrier gas flows through the drift tube in a direction generally opposing migration of ionized particles through the drift tube. The sample aerosol and carrier gas are introduced into the drift tube such that the sample aerosol circulates within the drift tube in a manner such that (a) a portion of the sample aerosol circulation is within a region of the drift tube to which an electrostatic field is capable of being applied for purposes of ion mobility separation and (b) a portion of the sample aerosol circulation is in a portion of the drift tube in which the electrostatic field, when applied, effectively blocks migration of additional ions into the separation region. The method further includes applying an electric field to the drift tube for purposes of ion mobility separation, wherein the application of the electric field increases the electrical potential of ionized particles with the sample circulation in the region of the drift tube to which the electrostatic field is applied. The ionized particles to which the electric field is applied migrate in the tube down a gradient of the applied field against the flow of the carrier gas to separate according to their ion mobility.

A seventeenth aspect is a method of the sixteenth aspect, further comprising detecting the separated ionized particles via a particle detector and correlating the detection of the particles with the timing of the application of the electric field.

An eighteenth aspect is a method of the sixteenth aspect, further comprising deactivating an electronic gate to allow at least a portion of the ionized particles to which the electric field is applied to pass through the gate, wherein the gate is positioned within the drift tube electrically downstream of the sample circulation region.

A nineteenth aspect is a method of the eighteenth aspect, further comprising detecting the separated ionized particles via a particle detector and correlating the detection of the particles with the timing of the deactivation of the gate A twentieth aspect is a method of any one of aspects 16-19, further comprising carrying the separated ionized particles via a stream of the carrier gas to a particle detector external to the drift tube.

A twenty-first aspect is a method of the twentieth aspect, wherein the separated ionized particles are carried in a conduit, and wherein the drift tube, the conduit and flow of carrier gas is configured to cause a portion of the carrier gas to flow in the drift tube against the migration of the ionized particles down the gradient of the electric field and to cause a portion of the carrier gas to flow in the conduit.

A twenty-second aspect is a method of any one of aspects 16-21, wherein the particle detector is a condensation particle counter.

A twenty-third aspect is a method of any one of aspects 16-22, wherein applying an electric field to the drift tube for purposes of ion mobility separation comprises applying the electric field such that a maximum voltage differential is achieved instantaneously or nearly instantaneously.

A twenty-fourth aspect is a method of any of aspects 16-22, wherein applying an electric field to the drift tube for purposes of ion mobility separation comprises applying the electric field such that voltage is ramped or stepped to a maximum voltage differential over a period of time.

A twenty-fifth aspect is a method of the twenty-fourth aspect, wherein the voltage is ramped or stepped to the maximum voltage differential over time.

A twenty-sixth aspect is a method of any one of aspects 16-25, wherein introducing the sample aerosol into the drift tube of the ion mobility spectrometer comprises obtaining precursor aerosol and modifying the precursor aerosol to form the sample aerosol.

A twenty-seventh aspect is a method according to the twenty-sixth aspect, wherein obtaining the precursor aerosol comprises selecting aerosol particles having a predetermined range of ion mobility.

A twenty-eighth aspect is a method according to the twenty-seventh aspect, wherein selecting the aerosol particles having the predetermined range of ion mobility comprises separating the particles via a differential mobility analyzer.

A twenty-ninth aspect is a method according to any one of aspects 26-29, wherein modifying the precursor aerosol comprises modifying the size, charge state, morphology or chemical composition of particles of the precursor aerosol to form the sample aerosol.

A thirtieth aspect is a method of any one of aspects 16-29, wherein the carrier gas introduced into the drift tube comprises vaporized liquid.

A thirty-first aspect is a drift tube ion mobility spectrometer configured to carry out a method of any one of the preceding aspects.

A thirty-second aspect is a system comprising the drift tube ion mobility spectrometer of the thirty-first aspect.

A thirty-third aspect is a system of the thirty-second aspect, further comprising a differential mobility analyzer device upstream of the drift tube, wherein the differential mobility analyzer is configured to allow flow of an aerosol comprising particles of a selected size range through the analyzer, and wherein introducing the sample aerosol into the drift tube comprises introducing the aerosol comprising the particles of the selected size range into the drift tube.

A thirty-fourth aspect is a system according to the thirty-second aspect, wherein the particles are of a size range of from about 2 nm to about 30 nm.

A thirty-fifth aspect is a system according to any one of aspects 30-32, further comprising a reaction cell downstream of the differential mobility analyzer device and upstream of the drift tube, wherein the reaction cell is configured to modify the particles of the aerosol that exit the differential mobility analyzer device prior to introduction in the drift tube.

A thirty-sixth aspect is a system according to the thirty-fifth aspect, wherein the reaction cell is configured to modify the size, charge state, morphology or chemical composition of particles of the aerosol.

A thirty-seventh aspect is a drift tube ion mobility spectrophotometer (DT-IMS) comprising: (i) a sample inlet; (ii) a drift tube through which ionized particles are configured to flow against a flow of a carrier gas; (iii) a carrier gas inlet; and (iv) a condensation particle counter (CPC) configured to detect the ionized particles that have drifted through the drift tube against the flow of the carrier gas.

A thirty-eighth aspect is a DT-IMS of the thirty-seventh aspect, further comprising a conduit configured to carry particles that migrate through the drift tube to the CPC.

A thirty-ninth aspect is a DT-IMS of the thirty-eighth aspect, wherein the carrier gas inlet, the conduit, and the drift tube are configured such that ionized particles that separate as they migrate towards the end of the drift tube are carried through the conduit by a stream of carrier gas, introduced through the carrier gas inlet.

A fortieth aspect is a DT-IMS comprising: (i) a drift tube through which ionized particles are configured to drift against a flow of a carrier gas; (ii) a detector positioned and configured to detect the ionized particles that have drifted through the drift tube against the flow of the carrier gas; (iii) a first plurality of electrodes disposed about the drift tube and configured to apply an electrostatic field having a voltage gradient along a longitudinal axis of the drift tube, along which gradient the ionized particles drift against the flow of the carrier gas; (iv) electronics operably coupled to the first plurality of electrodes and configured to control the electrostatic field applied via the electrodes; (v) a carrier gas inlet; and (vi) a sample inlet. The sample inlet, the drift tube, the electronics and the first plurality of electrodes are configured such that an aerosol introduced through the sample inlet circulates near a point in the drift tube where the voltage, in the direction of the longitudinal axis of the drift tube, is at zero when electrostatic field is applied via the first plurality of electrodes.

A forty-first aspect is a DT-IMS of the fortieth aspect, further comprising a conduit configured to carry particles that migrate through the drift tube to the detector.

A forty-second aspect is a DT-IMS of the forty-first aspect, wherein the carrier gas inlet, the conduit, and the drift tube are configured such that ionized particles that separate as they migrate towards the end of the drift tube are carried through the conduit by a stream of carrier gas, introduced through the carrier gas inlet.

A forty-third aspect is a DT-IMS of any one or aspects 40-42, wherein the detector is a condensation particle counter.

A forty-fourth aspect is a DT-IMS of any one of claims 40-43, further comprising a second plurality of electrodes disposed about the drift tube and configured to increase the electrical potential of ionized particles at the point in the drift tube where the voltage, in the direction of the longitudinal axis of the drift tube, is at zero when electrostatic field is applied via the first plurality of electrodes. The electronics are operably coupled to the second plurality of electrodes and are configured to control an electrostatic field applied via the second plurality of electrodes to increase the electrical potential of the ionized particles. One or more of the first plurality of electrodes are the same or different than one or more of the second plurality of electrodes.

A forty-fifth aspect is a DT-IMS according to the forty-fourth aspect further comprising an electronic gate positioned within the drift tube electrically downstream of the point in the drift tube where the voltage is at zero when electrostatic field is applied only via the first plurality of electrodes, wherein the electronic gate is operably coupled to the electronics.

A forty-sixth aspect is a DT-IMS according to any one of aspects 40-45, wherein the first plurality of electrodes and the electronics are configured to apply the electrostatic field in a constant manner, non-c manner, time invariant manner or time variant manner A forty-seventh aspect is a DT-IMS according to the forty-sixth aspect, wherein the first plurality of electrodes and the electronics are configured to apply an axially increasing, non-constant electrostatic field to focus ionized particles towards the longitudinal axis of the drift tube as the particles drift through the tube.

In a forty-eighth aspect a method for focusing ionized particles as they migrate down a voltage potential of a tube includes (i) introducing ionized particles into the tube, and (ii) applying an electrostatic field to a plurality of electrodes disposed around the tube. The electrostatic field has a gradient along a longitudinal axis of the tube, along which gradient the ionized particles migrate. The electrostatic field in the axial direction is increasing to focus the ionized particles towards the longitudinal axis of the tube as the particles migrate through the tube.

In a forty-ninth aspect, a device for focusing ionized particles includes (i) a tube having an inlet for introduction of the ionized particles and an outlet; (ii) a plurality of electrodes disposed about the drift tube and configured to apply an electrostatic field having a voltage gradient along a longitudinal axis of the drift tube, along which gradient the ionized particles migrate from the inlet to the outlet; (iii) and electronics operably coupled to the first plurality of electrodes and configured to control the electrostatic field applied via the electrodes such that the electrostatic field is increasing to focus the ionized particles towards the longitudinal axis of the tube as the particles migrate through the tube.

In the following, non-limiting examples are presented, which describe various embodiments of the articles, systems and methods discussed above.

EXAMPLES

Example 1

Development and Application of an Electrical Mobility Spectrometer

A. Abstract/Product Description

A measurement system that is able to measure deliquescence, efflorescence, and hygroscopic growth of particles down to 2 nm is proposed. The system makes use of a high resolution differential mobility analyzer in tandem with an ion mobility spectrometer (IMS) designed for use with charged aerosols. The advantages of this system include high resolution, low vapor consumption, and reduced diffusional losses. A prototype IMS coupled to a condensation particle counter (CPC) has been constructed and the device has shown good linearity response and high resolving power compared to existing technology. Further modifications to the device are described that should improve resolving power. The system may be used to measure, among other things, water vapor and particle interactions for furnace generated NaCl and $(NH_3)_2SO_4$ aerosols for sizes ranging from 2-20 nm. These results may be compared to existing experimental results for particles greater than 5.5 nm and to models for particles smaller than 5.5 nm where no experimental data exists.

B. Introduction

The Earth's atmosphere consists of an aerosol (solids and or liquids suspended in a gas) containing particles of different sizes, shapes, compositions, and concentrations. Understanding the properties of particles in atmospheric aerosols is necessary to determine the role they play in the environment including cloud formation (as cloud condensation nuclei) and haze. Aerosol particles interact with vapors in different ways based on the properties of the particles and the composition of the gas. The interactions of interest to this work are adsorption where vapor molecules are present on the surface of the particle and adsorption where the vapor molecules are present throughout the particle.

Previous research has shown that some atmospheric particles vary in size as a function of the relative humidity of the aerosol due to hygroscopic growth with or without deliquescence and efflorescence. Hygroscopic growth is a phenomenon where a particle swells to an increasing size as a function of the relative humidity. Deliquescence is described by a sudden jump in a particle diameter at a given relative humidity where a particle changes from a solid core with a saturated liquid shell to a saturated liquid solution. This deliquescence relative humidity (DRH) is based on the composition, temperature, size, and structure of the dry particle. Efflorescence is the reverse of deliquescence where nucleation of the solute in a saturated liquid particle occurs and the particle then shifts to a smaller size. Efflorescence occurs at a certain relative humidity (ERH) which is lower than the DRH.

Deliquescence occurs when the Gibbs free energy of the solid core/saturated shell is equal to the saturated solution. For given vapor and particle compositions the DRH and ERH are constant as a function of size for particles greater than ~100 nm. For particles less than 100 nm the Kelvin effect becomes important. The Kelvin effect takes into account the work done by the change in the surface area at a given surface tension. This effect raises both the DRH and ERH. For particles less than ~3 nm the surface tension deviates from bulk value adding a correction to the particle vapor pressure defined by the Kelvin effect. Several models exist to describe the deliquescence behavior of nanoparticles. These theories in general agree with experimental data although there is currently no experimental data to support the models below 5.5 nm.

Techniques for measuring deliquescence and hygroscopic growth of aerosol particles include Tandem Differential Mobility Analysis (TDMA), Atomic Force Microscopy (AFM), Electro-Dynamic Balances (EDB), Raman Spectroscopy, Ion Mobility Spectroscopy Mass Spectrometry (IMSMS), and Environmental Scanning Electron Microscopy (E-SEM). The TDMA technique has been able to measure the size effects on DRH and ERH to the smallest sizes, down to ~5.5 nm. TDMA consists of three major components. The first is a differential mobility analyzer (DMA) that is used to select a near monodisperse charged particle size based on the electrical mobility $Z_p$ of the particles. A particle's electrical mobility is a function of the particle diameter, number of charges, and gas properties as shown in Equation 9.

$$Z_p = \frac{neC_c}{3\pi\mu D_p} \quad (9)$$

Where n is the charge number, e is the unit charge, $C_c$ is the slip correction factor (important for ions in the transition regime), μ is viscosity, and $D_p$ is the particle diameter. The velocity of an ion in an electrostatic field $\bar{E}$ is $\bar{v}=Z_p\bar{E}$. The aerosol is then passed through a reaction region where the RH of the aerosol is increased or decreased to a set value. The third component is a particle spectrometer consisting of a second DMA and particle detector that determines the particle concentration at various mobilities selected by the second DMA.

A limitation of the TDMA technique for measuring the DRH and ERH of nanoparticles is the transmission efficiency of the system. As the size of the particle decreases the diffusion coefficient increases according to Einstein's relation. The increased diffusion coefficient leads to increased losses to the walls of the humidification/evaporation section and the transfer tubing as well as causing increased broadening of the diameters selected by the first DMA. Additional experimental errors arise from the fact that DMA selected aerosol is not truly monodisperse. The variability in the diameters present can lead to bi-modal deliquescence and complications in interpreting the data. The minimum detected size for the detector used after the second DMA is also a limitation for the system.

A desired system for measuring the deliquescence of nanometer scale particles may have the following features:
- The size selected aerosol having a small standard deviation in size. This can be accomplished by either a high resolution DMA or by investigating large molecular ions of a single mobility.
- The amount of gas required (drift gas including reaction vapor) being close to the sampled aerosol volume. In current TDMA systems the drift gas flowrate required is often ten times the aerosol flowrate.
- The mobility selector, transport lines, reactor, and mobility analyzer having minimal diffusion losses i.e. short lengths. Current systems require additional transport lengths in the reaction region to allow equilibrium of the aerosol with the tube walls.
- The mobility analyzer having a high resolution allowing measurement of small changes in particle size. Resolving powers of commercial DMAs are near 20 and powers greater than 50 have been achieved with specialized laboratory analyzers. Accounting for experimental errors current systems can measure mobility diameters to a precision of 0.3%. This limits the detection of the formation of a monolayer to particles smaller than 200 nm.
- The mobility analyzer detector having high sensitivity to enable measurement of low concentration aerosols. State of the art electrometers can measure the net difference of all charged particles present in an aerosol with currents ranging in femptoamps (1e-15 amps) which corresponds to 1e4 charges/ions per second. Condensation particle counters are able to count single particles and commercially available counters are unable to detect particle diameters less than 2 nm.
- If the second mobility analyzer is used as the reaction chamber i.e. the particle undergoes deliquescence, efflorescence, or hygroscopic growth inside the device, the following additional features are desired: the particles reside in the test aerosol gas for a negligible amount of time compared to the drift time through the spectrometer, the particle experiences a near constant electrostatic field, and the reaction time is negligibly small compared to the drift time. Differential mobility analyzers currently used in TDMA do not have negligible residence times in the aerosol gas and transit velocities are not constant due to the varying filed along the particle trajectory.

The system can be operated at atmospheric pressure

For this work a novel measurement system is proposed that will enable measurement of deliquescence and hygroscopic growth of particles down to 2 nm by addressing limitations of current systems.

C. System Overview

To address several of the goals of the measurement system a novel application of a drift tube type ion mobility spectrometer is proposed for the reaction region and downstream mobility spectrometer. In Ion Mobility Spectroscopy (IMS) charged particles (ions) are introduced at one end of a tube in a "packet" that is created by an electric gate device. The ions then travel in the direction of a constant axial electric field and reach the other end of the tube at different times based on their electrical mobility $Z_p$.

The advantages of ion mobility spectrometers include high resolving power (can exceed 100), low drift gas volume, and separation of the particles from the carrier aerosol into the drift gas at the start of the mobility separation. The fact that the ions spend the majority of the drift time in the drift gas allows for the spectrometer to be used as the reaction region. Since the electric field is constant it also simplifies any corrections required for non-negligible reaction times. Disadvantages of existing ion mobility spectrometers include low sensitivity due to the use of an electrometer as the ion detector. Additionally the shutter mechanism in ion mobility spectrometers require the ions to pass through an array of wires which leads to losses of ions through diffusional deposition. Current IMS technology does not allow sampling of pre-charged ions which makes their application in tandem configurations not possible without modification to the sample introduction technique. Design of a IMS for this application including modifications to address the limitations of traditional IMS operation is discussed below.

D. Preliminary Research: Simulations and Design

Figure 17:
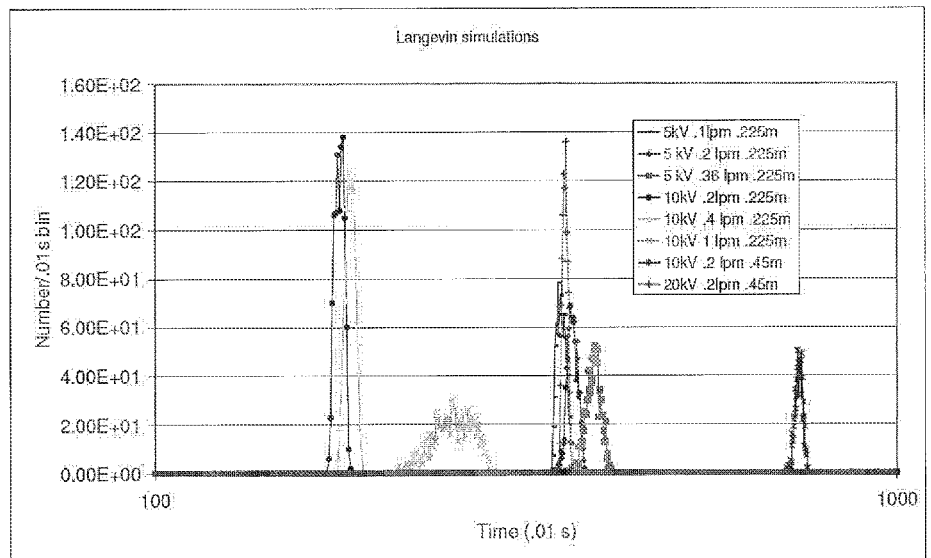
FIG. 17 is a plot of Langevin simulations of IMS.

Design of a prototype ion mobility spectrometer utilized simulation tools to map particle trajectories, fluid flow, and electrostatic fields. These simulation tools along with analytical expressions for determining resolving power $\Delta t/t_d$ were used to determine the geometry of the prototype device and to determine what parameters affected the overall resolving power. The analytical expression used to calculate the resolving power is given by Equation 10

$$(\Delta t)^2 = (\Delta t_0)^2 + \left(\frac{16kT\ln 2}{Ve}\right)\frac{t_d^2}{z} \quad (10)$$

Where $\Delta t_0$ is the half width of the input pulse time, V is the drift tube voltage, e is the unit charge, z in the number of charges, k is Boltzmann's constant, T is temperature, and $t_d$ is the drift time. This equation shows that the resolving power is independent of particle mobility and increases only with voltage. Fluid flow and electrostatic fields were modeled in Fluent software and particle paths were modeled using a user defined function in Fluent and using code written in Fortran. Both programs applied the Langevin equation to define particle trajectories given by Equation 11.

$$m\vec{v} = \vec{F} - m\beta\vec{v} + \vec{X} \quad (11)$$

Where β is the friction factor/particle mass and X is the random force. The Fortran code applied an algorithm to solve the Langevin equation using an algorithm given by Ermak and Buckholtz. FIG. 17 shows simulation results for several different voltages, drift tube flowrates, and drift lengths. All of the simulations used particle diameters of 7.8 nm, drift tube diameter at 4 cm, and the flow profile modeled as fully developed laminar. The simulations did not model a timed gate but instead modeled randomly selected starting points in a packet 1 cm in length and 2 cm diameter at the start of the electric field. This length can be converted to pulse time using $\Delta t_0 = \Delta x_0/Z_p E$ where $Z_p$ is the electrical mobility of the particle, E is the electric field, and $\Delta x_0$ is the packet length. The device length can be converted to drift time using a similar equation where $td = L/ZpE$ where L is the drift tube length.

Figure 18:
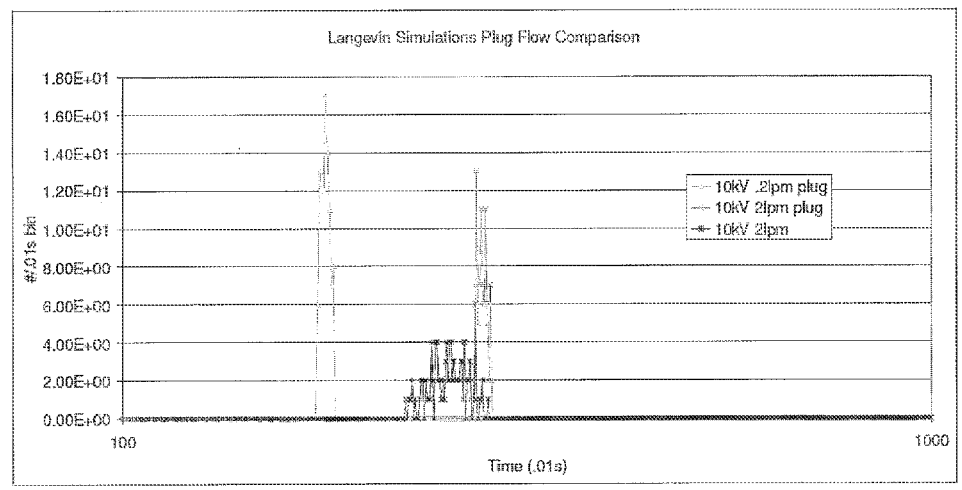
FIG. 18 is a plot of Langevin simulations of plug flow comparisons.

The simulation results verify the change in resolving power (t/Δt) with varying drift tube length with values near 20 for the shorter tube and near 40 for the longer (for similar field strength and low drift gas to ion drift velocity ratios). The simulations also show that increasing the drift tube flowrate causes the resolving power to drop. To investigate the cause of the reduced resolving power the model was run using a plug flow profile. FIG. 18 shows that peak broadening increases at a lower rate using plug flow which confirms that the source of broadening is due to the variability in the flow velocity in the radial direction for fully developed laminar flow. In order to reduce this effect in an instrument design either the sample can be confined towards the center of the tube or the drift velocity must me considerably greater than the gas velocity.

A goal of this device is to have high ion detection sensitivity. To achieve this a condensation particle counter device (CPC) (TSI Model 3786) was used as the detector. The major advantage of this type of detector is the ability to count single particles. Disadvantages include needing to be operated near atmospheric pressure, particle size sensitivity (detection of 50% of particles at ~2.5 nm), and upper concentration limit of 100,000 particles/cm$^3$ (specifications from instrument brochure). The response time of the CPC can lead to broadening of peaks whose time constants and drift/delay times are similar to that of the CPC. Inside the device the detector sampling port was designed to minimize disturbance of the field and to maximize transport of ions to the inlet. Additionally the detector requires a sample flow in contrast to the faraday cups used in commercial IMS devices. To address this, a gas is introduced at the end of the drift tube at a flowrate that is equal to the detector flow plus the drift gas flow. FIG. 8 shows flow pathlines of the drift and detector gas in red and pathlines of 10 nm particles in blue.

Figure 19:
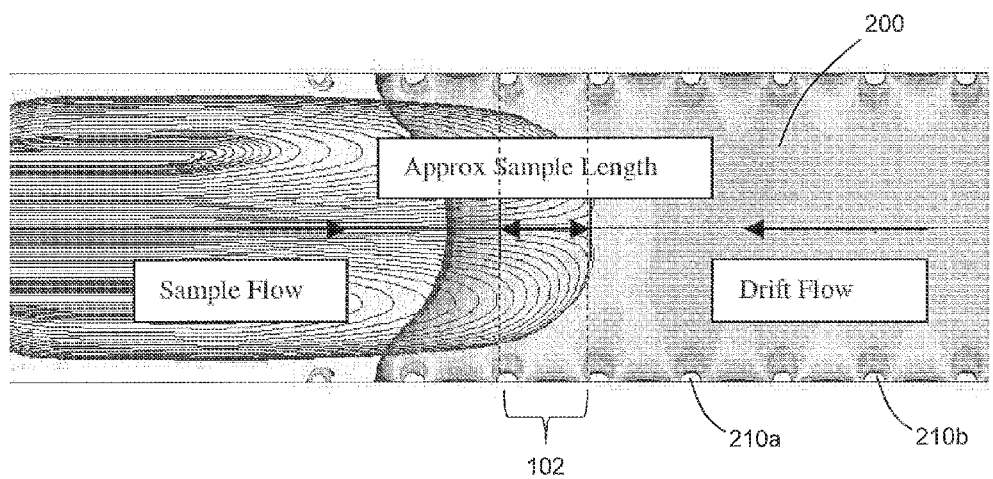
FIG. 19 is a schematic image of a simulation of sample flow pathlines and electrostatic contours in a portion of a DT-IMS in which charged particles of the sample may be captured. The field contours range from −100 kV/m to 0 kV/m.

To address diffusional losses in a sample gate a "gateless:" sample introduction scheme can be used. In this configuration the aerosol is introduced in a circulating pattern near a point in the device where the electrostatic field in the axial direction is at zero. At the start of analysis the voltage is applied to the electrodes and only aerosol particles that are downstream of the zero point are sampled. FIG. 19 shows the sample flow pathlines superimposed on the electrostatic field. Note that the edge of the electrostatic field contours indicates the zero field boundary. In FIG. 19, the drift tube 200, capture zone 102, and spacers 210a and 210b that separate axially aligned rings (not shown) are labeled.

An overall schematic of the device is shown in FIG. 12. The instrument utilized a modified uni-polar charger (UPC) device for the electrodes and main housing. Modifications to the UPC included the inlet and exit diffusers and the mounts for the sample inlet and detector. The diffusers consist of open cell acoustic foam mounted onto custom fabricated plastic alignment pieces to center the tubes on each end.

The two main performance features of a viable IMS-CPC is the linearity of the drift time to particle $Z_p$ across different operating conditions and resolving power. The linearity experiments used NaCl particles generated using a tube furnace with an aerosol flow rate ranging from 1-2 liter/minute. The aerosol generator utilized a recirculating quench gas flow at 3 liter/minute. The aerosol was then passed through an aerosol neutralizer containing a Po-210 radioactive source. The neutralizer gives the test aerosol a known charge distribution allowing for electrical mobility separation. Aerosol particles were mobility selected using a TSI Model 3085 NanoDMA with a sheath flowrate of 15 liters per minute (lpm) and a sample flowrate of 0.6 lpm unless specified. The instrument flowrates for the majority of the experiments are shown in Table 1. The given flows resulted in a drift gas flow rate of 0.2 lpm and a drift velocity of 0.0052 meter/second along the centerline. The drift gas flow rate was chosen arbitrarily. The error in the drift flow rate is 5% if the errors in the detector flows are assumed to be 1% each. A diagram of the experimental setup is shown in FIG. 16.

TABLE 1

Experimental Parameters

| Location | Flow rate (liter/minute) |
|---|---|
| Sample Inlet | 0.6 in |
| Sample Excess | 0.8 out |
| Detector Sheath | 0.8 in |
| Detector Inlet | 0.6 out |

Figure 20:
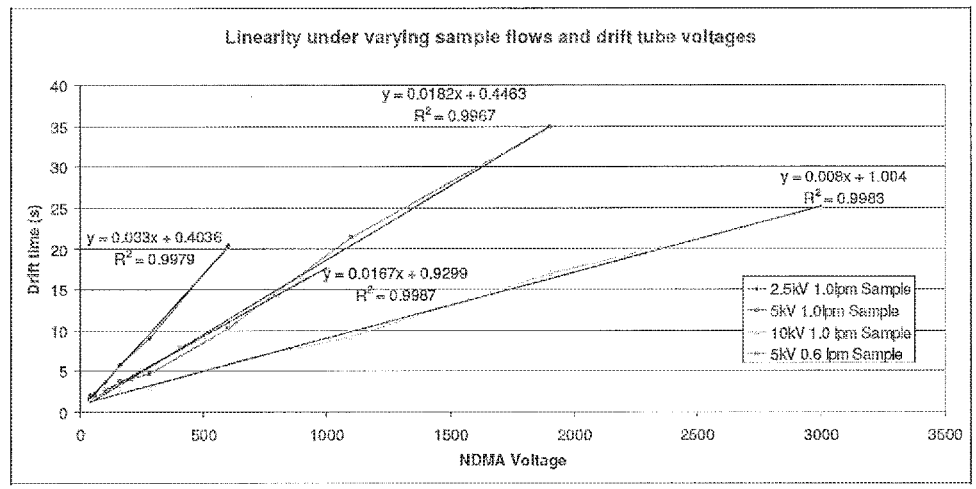
FIG. 20 is a plot showing linearity under varying sample flows and drift tube voltages in a test DT-IMS system.

To investigate the linearity of the device the peak drift time was measured for several different mobilities. The temperature of the tube furnace was adjusted for each calibration point and the selected mobility was set at the peak mobility leaving the furnace. This was done to minimize errors in the peak mobility that can occur when the input aerosol to a DMA has a sloping variability in mobility. The results from the linearity experiments are shown in FIG. 20. The data show R$^2$ values greater than 99% for the conditions tested.

Figure 21:
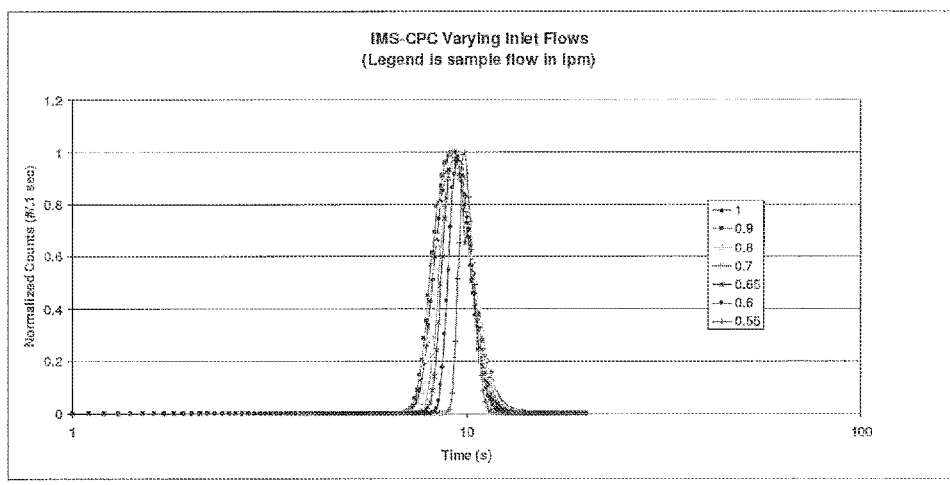
FIG. 21 is a plot of ion detection at various sample flow rates in a DT-IMS-CPC system.

High resolution mobility spectrometers typically use high molecular weight ions as the standard for measuring resolving power. Unfortunately the condensation particle counter used in the device is unable to detect these ions. Due to this limitation the resolving power was investigated by varying the IMS sample inlet flow rate effectively shortening the introduced sample length. For the sample inlet flow experiments the NanoDMA sample flowrate was fixed at 1.0 lpm to keep the sample aerosol consistent. In general the resolving powers of DMAs are equivalent to the flow ratios when particle diffusion can be neglected although others showed that the maximum resolving power approaches about 17 (D. R. Chen and D. Y. H. Pui, "A High Efficiency, High Throughput Unipolar Aerosol Charger for Nanoparticles," *Journal of Nanoparticle Research*, vol. 1, pp. 115-126, 1999). The results shown in FIG. 21 indicate that the resolving power of the device varies strongly with the sample flowrate (which effectively changes the sample length). For the lowest sample inlet flow i.e. shortest length the resolving power is measured at 11.1 (using a detector delay time of 1 second) and the resolving power of the DMA is estimated to be less than 15. This implies qualitatively that the resolving power of the IMS is considerably higher than the NanoDMA resolving power.

The results of the preliminary research show the feasibility of this device for measuring mobility distributions of aerosols and provides a basis for continuing research.

Further optimization of the geometry and operating conditions including modifications to the sample introduction scheme, voltage scheme, etc. may be readily made by those of skill in the art upon reading the disclosure presented herein. Simulations that include analytical solutions to the mobility distributions resulting from the particle transfer function of this device in a tandem measurement system may be used for purposes of optimization. The resolving power of the device and measurement of DRH, ERH, and hygroscopic growth of nanometer scale particles, among other things, may be investigated. Some discussion of additional simulations and optimization that may be performed are discussed below.

E. Simulations and Design

Figure 22:
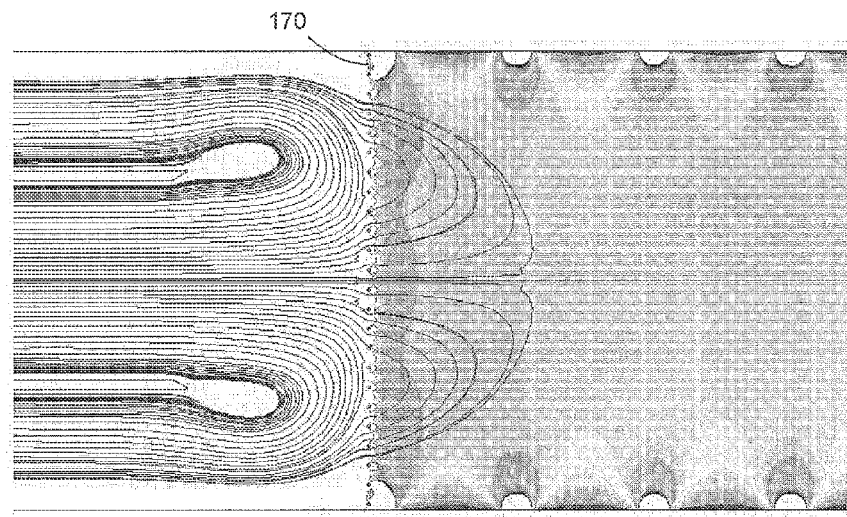
FIG. 22 is a schematic image of a simulation of sample flow pathlines and axial electrostatic field contours in a portion of a DT-IMS in which charged particles of the sample may be captured. The DT-IMS includes a screen. The field contours range from −100 kV/m to 0 kV/m.

While the gateless sample introduction is helpful for limiting diffusional losses the zero field contour is not flat in the radial direction and the gradient near the boundary is not sharp (see FIG. 22). These two drawbacks lead to size dependent resolution and overall lower resolution. The size dependent resolution stems from the idea that particles with lower mobilities will require a stronger E-field to overcome the drift gas flow than lower mobility particles. The non-flat contour leads to a wider variability in particle starting points i.e. longer sample length which proportionally affects the resolving power. To address this issue a wire mesh is placed across the tube to help define a sharper sample packet. The additional diffusion losses due to the screen may be considered in the transfer function calculation. Additional modeling and experimental work may be done to minimize the drift tube flow rate. FIG. 22 shows the pathline and field contours when a screen 170 is present.

For such a device to provide useful results it may be important to map the probability distribution of measured mobility for a given input mobility. Variances in the measured mobility arise from size dependent diffusional losses, diffusional broadening, DMA transfer function, IMS sample introduction length and diffusion broadening, and detector time constants. The resulting transfer function preferably provides for a given measurement time the distribution of mobilities being detected. The mathematical representation of an overall transfer function is shown in equation 12.

$$N(t) = \int_0^\infty \int_0^\infty n_0 \eta_{Sa} \Omega_{DMA} \eta_{Xfer} \eta_{Gate} \Delta_{RXN} \Omega_{IMS} \eta_{Det} dZ_p dt \quad (12)$$

Where $n_0(Z_p)$ is the input aerosol concentration. Where $\eta_{Sa}(Z_p, Q_{sa}, L)$ is the penetration through a sample tube length L at a flow rate $Q_{Sa}$. Where $\Omega_{DMA}(Z_p, \beta)$ is the transfer function of the DMA where $\beta$ is the ratio of sample to sheath flows. The diffusional losses between the DMA and the start of the drift region are $\eta_{Xfer}(Z_p, Q_{Sa}, L)$ and $\eta_{Gate}(Z_p, Q_{Sa})$ respectively. The two penetrations are found using different equations and are therefore separated. The $\Delta_{RXN}(Z_p, n_v)$ term accounts for vapor-particle reactions where $n_v$ is the vapor concentration. The reaction term assumes that all particles are spherical and of the same composition and charge state. The IMS contribution is given by $\Omega_{IMS}(Z_p, V, t_{Gate})$ where V is the drift tube voltage and $t_{gate}$ is the sample pulse time i.e. the sample length. The penetration and diffusional broadening of the detector is given by $\eta_{Det}(Z_p, t)$. The detector introduces two mobility dependent errors, one is due to mobility dependent diffusional losses to the tube walls and the other is axial diffusion down the length of the device which leads to time dependent errors. The equations that may be used to define each of the transfer function terms are described below:

$\eta_{Sa}(Z_p, Q_{Sa}, L)$, $\eta_{Xfer}(Z_p, Q_{Sa}, L)$—The penetration through sample tubes is calculated using equations given by Hinds and is shown in equations 13 and 14.

$$P_{\mu<0.009} = \frac{n_{out}}{n_{in}} = 1 - 5.50\mu^{2/3} + 3.77\mu \quad (13)$$

$$P_{\mu \geq 0.009} = 0.819 e^{-11.5\mu} + 0.0975 e^{-70.1\mu} \quad (14)$$

Where $$\mu = \frac{k_B T Z_P}{Q_{Sa} e}.$$

and n is the number concentration.

$\Omega_{DMA}(Z_p, Z_{Pi}, \Delta Z_{Pi})$—The transfer function of the DMA. The equations calculate a probability distribution of mobilities for a given set of fixed DMA operating conditions. The diffusion neglected equation for a DMA transfer function is given by Knutson and Whitby and is shown in equation 15 (E. O. Knutson and K. T. Whitby, "Aerosol classification by electric mobility: apparatus, theory, and applications," *Journal of Aerosol Science*, vol. 6, pp. 443-451, 1975.).

$$\Omega = \begin{cases} 0 & -\infty \leq Z_P \leq Z_{Pi} - \Delta Z_{Pi} \\ Z_P/\Delta Z_{Pi} - (Z_{Pi}/\Delta Z_{Pi} - 1) & Z_{Pi} - \Delta Z_{Pi} \leq Z_P \leq Z_{Pi} \\ -Z_P/\Delta Z_{Pi} + (Z_{Pi}/\Delta Z_{Pi} - 1) & Z_{Pi} \leq Z_{Pi} \leq Z_P + \Delta Z_{Pi} \\ 0 & Z_{Pi} + \Delta Z_{Pi} \leq Z_P \leq -\infty \end{cases} \quad (15)$$

Where $Z_{Pi}$=the peak mobility=$q_{sh}/2\pi\Lambda f V i$, $\Delta Z_{Pi}=q_{sa}/2\pi\Lambda V i$, Vi is applied voltage, $q_{sh}$ and $q_{sa}$ are the sheath and sample flowrates respectively, and $\Lambda=L/\ln(b/a)$ where L is DMA length and a and b are the center rod and outer tube radii. The resulting transfer function is a triangle centered on $Z_{Pi}$ with a base half width of $\Delta Z_{Pi}$. When diffusion effects are not neglected the transfer function takes on a Gaussian shape and the probability of particles with a mobility of $Z_{Pi}$ leaving the DMA under a fixed set of operating conditions is less than 1.

$\eta_{Gate}(Z_p, Q_{Sa})$—Diffusion losses to the gate. The gate in this device consists of a wire mesh. Diffusion losses of particles through meshes has been developed by Cheng et al. and is shown in equation 16 (D. R. Chen, et al., "Design and evaluation of a nanometer aerosol differential mobility analyzer (Nano-DMA)," *Journal of Aerosol Science*, vol. 29, pp. 497-509, June-July 1998).

$$P = \exp\left(\frac{-10.8\alpha h P e^{2/3}}{\pi(1-\alpha)d_f}\right) \quad (16)$$

Where α is the solid fraction, h is the solid height, Pe is the Peclet number (Udf/D) where df is the fiber diameter and U is the free stream velocity. The screen used for this device is a 15×15 mesh with a 0.010" (2.54e-4 m) diameter fiber radius. This gives h=5e-4 m and α=0.12. The penetration through the gate is near 100% for particles at 25 nm and 73% for 1 nm.

$\Delta_{RXN}(Z_p, n_v)$—Change in mobility due to reactions. This factor is unknown and is determined by deconvoluting the output with the transfer function.

Figure 23:
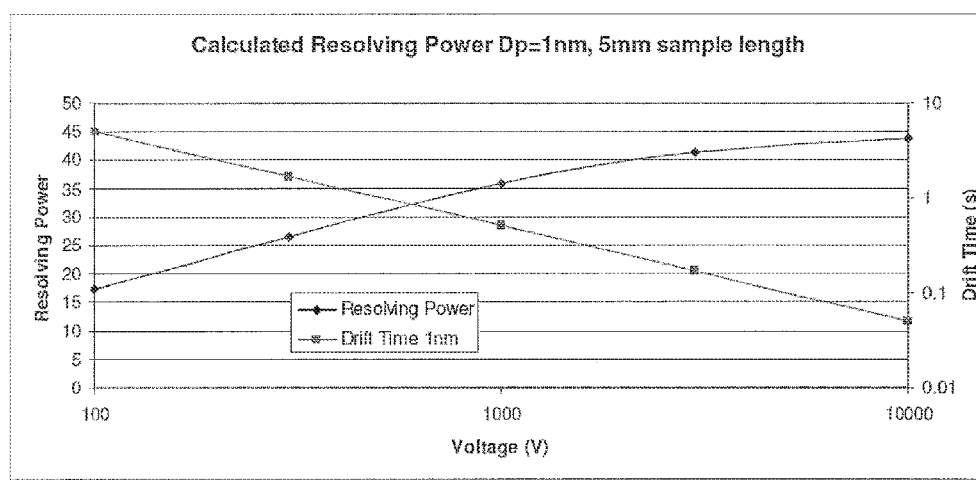
FIG. 23 is a plot of calculated resolving power as a function of voltage for a test DT-IMS device.

$\Omega_{IMS}(Z_p, V, t_{Gate})$—The distribution of time for a given Zp in the IMS. Once the aerosol sample enters the IMS time becomes a variable of concern. If the drift tube velocity is neglected i.e. the drift gas velocity is much less than the particle drift velocity and the sample introduction is assumed to input a normally distributed pulse i.e. $n(x) = n(v_{drift}*t)$=normally distributed, then the pulse half width at a plane at the end of the drift tube is given by equation 17:

$$(\Delta t)^2 = (\Delta t_0)^2 + \left(\frac{16kT\ln 2}{Ve}\right)\frac{t_d^2}{z} \quad (17)$$

Where $\Delta t_0$ is the half width of the input pulse, V is the drift tube voltage, e is the unit charge, z in the number of charges, k is Boltzmann's constant, T is temperature, and td is the drift time. The drift time td is given by $L/v_{drift}$ where $v_{drift}$ is given by $Z_p E$ and E is V/L. This simplifies to $t_d = L^2/ZPV$, where L is the drift length and V is the voltage. The resolving power is given by $\Delta t/t_d$. FIG. 23 shows a plot of estimated resolving power and drift time for the prototype device operated at different voltages.

If the $\Delta t_0$ is assumed to be a fixed length versus a time then the resolving power is constant for all mobilities. For L=0.225 m and $\Delta x$=0.005 m at 10 kV the resulting resolving power is 44 if diffusion in the detector is neglected. This leads to a desired gating scheme that does not alter the sample packet length as a function of mobility i.e. shutters particles that are traveling at a low velocity e.g. carried with the sample gas. The drift gas velocity can be neglected for high mobility particles but for the operating parameters described above at 20 nm the drift velocity approaches 25% of the drift gas counterflow velocity. The $\Delta t$ equation with this correction is given in Equation 18. It can be seen from this equation that increased drift velocity will lead to increased $\Delta t$ therefore a lower resolving power. Note that this equation assumes plug flow. Additional broadening will arise if a fully developed flow profile is considered. This effect is shown in the simulation results in FIG. 18.

$$(\Delta t)^2 = (\Delta t_0)^2 + \frac{16kTZ_p t_d \ln 2}{ze(Z_P E - u_{drift})^2} \quad (18)$$

$\eta_{Det}(Z_p, t)$—Diffusional losses and axial diffusional broadening in the detector. Diffusional losses in the detector follow the same losses described above for tubes. Since the detector is in the time domain there is also a correction required for axial diffusion. The equations for this effect adds an additional term to equation 19 which gives $$(\Delta t)^2 = (\Delta t_0)^2 + \left(\frac{16kT\ln 2}{Ve}\right)\frac{t_d^2}{z} + \frac{16Dt_{det}(\ln 2)}{v_{det}^2} \quad (19) \; 11$$

where $t_{det}$ is the residence time in the detector and $v_{det}$ is the average flow velocity in the detector tube.

The transfer function of the system can be applied to two cases, generation of molecular ions of a single mobility and sampling from a polydisperse input aerosol. For the molecular ion case since the drift time is a linear function of $Z_p$ the transfer function is a Gaussian with $\sigma^{1/2}(Z_p)=m\Delta t$ where $\sigma^{1/2}$ is the half width and m is the slope of the calibration curve. If the drift gas is neglected and the voltage error is considered to be 1% and the length error is considered to be 1% (due to errors in_x0) then the error in peak mobility is 1.4%. In cases where the input aerosol is polydisperse the system transfer function must consider the transfer function of the first DMA. An analytical expression for the system transfer function may be determined as part of the proposed work. This analytical expression may include variables that can be used to fit experimental data to the analytical expression. These variables may account for imperfections in the device including flow variability, sample shape, DMA imperfections and others. The analytical expression can ultimately be used to iteratively determine the input aerosol distribution based on the output results.

The limitations for resolving power and minimum particle size are affected by the detector properties and it may be desirable to develop a fast mixing condensation particle counter that is able to achieve high saturation ratios of the working fluid. The time response performance goals for the device would be similar to a CPC developed by Flagan and co-workers. The target minimum detected size may be, for example, less than 1 nm which has been previously achieved with a mixing type CPC. The analytical expression for the transfer function may be used to determine the necessary detector properties. Measurement of these properties is discussed in the experimental section.

F. Experimental

The experimental work for this device may include verification of the resolving power and transfer function. Application experiments may include measurement of mobility shifts due to vapor adsorption and absorption for various combinations of particle materials, sizes, and vapor concentrations.

The resolving power of an IMS device increases with operating voltage as shown in FIG. 23. The maximum operating voltage is limited by geometry in the case of arcing and by the response time of the detector (as the voltage increases the value for $\Delta t$ decreases). Experiments to measure the resolving power of the device may be done using Tetra-Alkyl molecular ions generated via electrospray. These compounds are beneficial since they produce ions of a single mobility. The disadvantage is they are too small to be seen by conventional condensation particle counters (unpublished data by McMurry group). The detectors that are able to see these ions include faraday cage type electrometers and a diethylene glycol CPC that was developed by the McMurry group at the University of Minnesota. A fast response electrometer that utilizes electrostatic precipitation of the ions may be developed for use in these experiments. To determine the response time characteristics of potential detectors an electrostatic precipitator may be fabricated that may be able to rapidly change the aerosol concentration at the detector inlet. Results from these experiments may give the delay time and the time constant of the detectors. These values can be used to determine the theoretical resolving power of the IMS coupled to each detector.

The resolving power measurements may be performed at several IMS operating voltages and inlet flow rates (i.e. initial sample length). These data can then be used to back out the value that can be used for $\Delta t_0$. These data can then be used to fit constants that were determined for the analytical expression for the system transfer function excluding the first DMA. Additional experiments may then be run using polydisperse aerosol generated via a tube furnace. The results may then be used to determine the correction constants in the first DMA. The correction constants may be compared to previously published data for the DMA.

One proposed application of this device is to measure the adsorption of vapors onto the surface of particles in the range of 2-20 nm. The advantages of using this device over previous technology include high resolving power at low sheath/drift gas flow rates and a nearly instant exposure to the vapor at the start of mobility separation. The experimental measurements that may be performed may measure the shift in mobility of particles at varying water vapor concentrations. The particle materials may include furnace generated NaCl and $(NH_4)_2SO_4$ utilizing a conditioning system that cause the particles to deliquesce and effloresce prior to sampling ensuring the particles consist of a single crystal. The furnace generated aerosol reduces errors due to particle contamination seen in nebulized source aerosols. The vapor concentrations may be set using a humidity control system developed for the NanoTDMA system at the University of Minnesota. Experiments may focus on measurement of the relative humidity at the point of deliquescence for NaCl and $(NH_4)_2SO_4$ and the results may be compared to values that have been measured by several researchers. Measurements of sizes smaller than 6 nm may be compared to theories developed by Russell and Ming (L. M. Russell and Y. Ming, "Deliquescence of small particles," *Journal of Chemical Physics*, vol. 116, pp. 311-321, Jan. 1, 2002) and McGraw and Lewis (R. McGraw and E. R. Lewis, "Deliquescence and efflorescence of small particles," *Journal of Chemical Physics*, vol. 131, Nov. 21, 2009) and to molecular dynamics simulations done by Russell and Bahadur (R. Bahadur and L. M. Russell, "Water uptake coefficients and deliquescence of NaCl nanoparticles at atmospheric relative humidities from molecular dynamics simulations," *Journal of Chemical Physics, vol.* 129, Sep. 7, 2008). These experiments require that equilibrium is quickly reached in the device and the results will indicate if errors due to equilibration time can be neglected or show that an additional correction is needed or desired. To investigate this, the measurements may be made at several drift voltages. Changes in the measured mobility diameter may indicate a reaction time dependence. Molecular dynamics simulations of deliquescence show that the time to reach equilibrium ranges from 1 to 65 μs for NaCl particles 1-11 nm in diameter which is short compared to the theoretical drift times which are on the order of ms.

The results of these experiments and the development of this device will be valuable for researchers investigating growth of freshly nucleated atmospheric aerosols due to adsorption of water vapor. They may also provide the first opportunity to test deliquescence models down to 2 nm.

G. Conclusion

A device that is able to measure the electrical mobility of aerosols with high resolving power across a wide range of mobilities has been developed and initial experimental data show that the performance of the device is near what is theoretically expected. Modifications that may improve the device performance include an alternate sample introduction technique, modification of voltage schemes, and minimization of the detector response time. A transfer function for the device in a tandem arrangement was shown and a solution to the function is proposed herein. Experiments for the device may focus on measurement of the shift in particle mobility due to the absorption and adsorption of water vapor onto particles as a function of the vapor concentration, particle size, and particle composition. These data may be taken for a smaller size range than previously investigated and compared to models for predicted behavior.

Example 2

Figure 24:
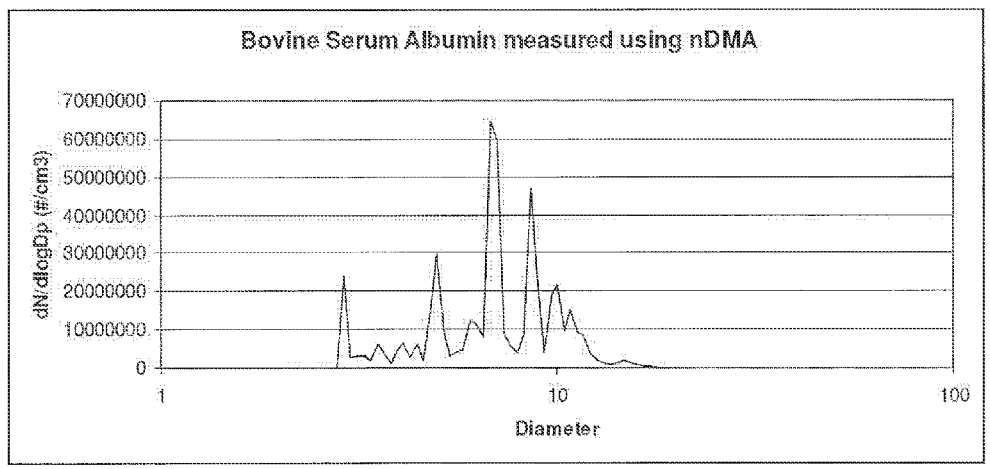
FIG. 24 is a plot of ion detection of electrospray generated BSA measured using a nDMA.

Measurements of Mobility Distributions of Electrosprayed Protein Solutions Using the DT-IMS The prototype DT-IMS was used to measure the electrical mobility of Bovine Serum Albumin particles generated via electrospray ionization (TSI 3480). The measured mobility distribution can be compared to published measurements made using a High Resolution Differential Mobility Analyzer (HR-DMA) and measurements made using a Nano-Differential Mobility Analyzer (nDMA, TSI 3085). The results from the nDMA measurements are shown in FIG. 24.

Figure 25:
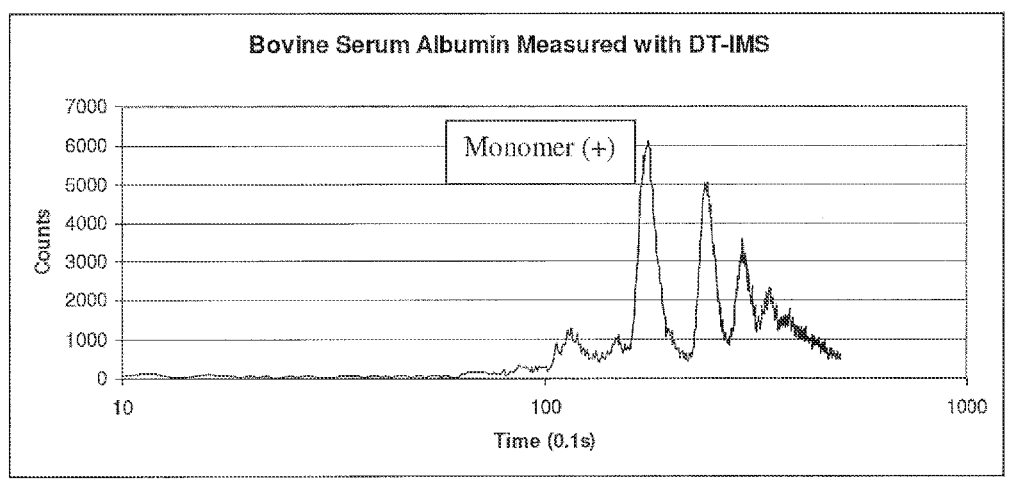
FIG. 25 is a plot of ion detection of electrospray generated BSA measured using a test DT-IMS.

FIG. 25 shows a mobility measurement using the DT-IMS. Qualitative agreement is evident compared to DMA measurements. Note that the nDMA data is corrected for charging efficiency which is lower for smaller particles (thereby increasing peak heights for small particles in the corrected data).

Figure 26:
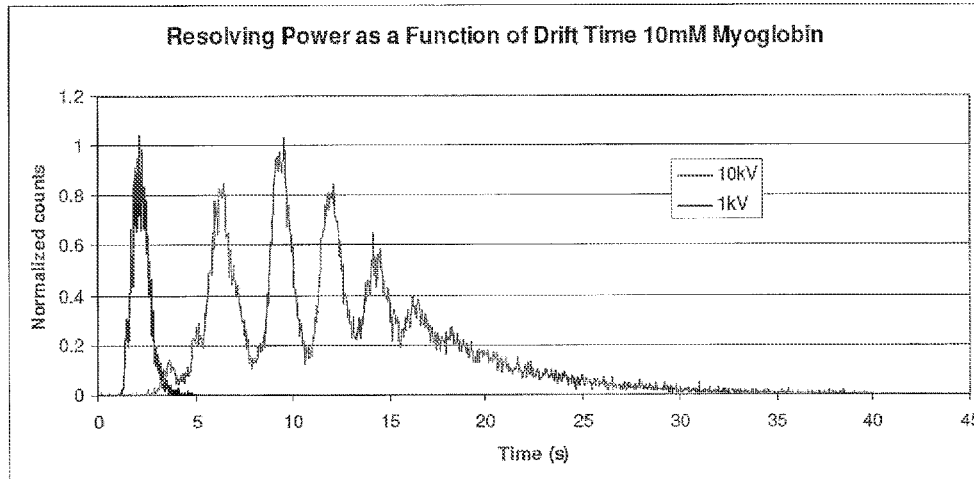
FIG. 26 is a plot of resolving power of myoglobin mobility distributions at different voltages as a function of drift time using a test DT-IMS.
Figure 27:
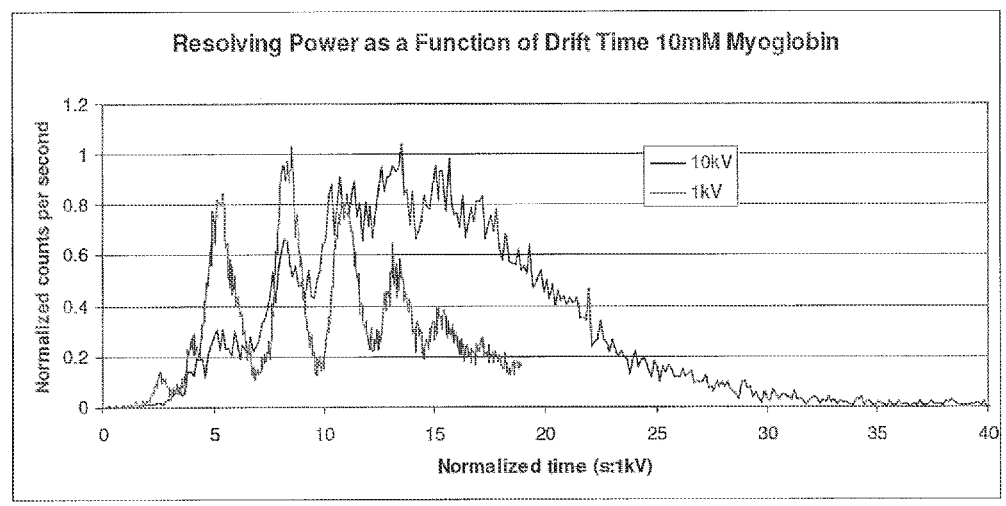
FIG. 27 is a plot of resolving power of normalized myoglobin mobility distributions at different voltages as a function of drift time using a test DT-IMS.

To demonstrate the speed of the device measurements of electrosprayed Myoglobin were made at different drift voltages. FIG. 26 shows mobility measurements made at 10 and 1 kV. FIG. 27 shows the same data with the time axis normalized to the 1 kV scan. For comparison the nDMA results shown above had a 120 second scan time. The HR-DMA scan times were on the order of 300 seconds.

Initial tests show that as the measurement time is reduced the resolving power of the instrument decreases. Theoretically the opposite is true. We suspect the observed loss of resolution is due to the long response time of the CPC used (TSI 3786) compared to the time between peaks. A faster detector may be able to better resolve the peaks at low scan times.

Summary, Overview and Additional Experimentation

A new drift tube type Ion Mobility Spectrometer (DT-IMS) has been designed and may be particularly useful for aerosol particle measurements from ambient environments. DT-IMS devices allow for determination of the electrical mobility of a charged particle through measurement of the time necessary for a particle to travel a fixed distance through a tube in the presence of an electrostatic gradient. These instruments have traditionally been limited to measurements of ionized molecules and small (~1 nm) charged clusters. Previously developed devices are not able to sample charged aerosol particles from the ambient because of the high electric fields present at the beginning of the drift region. An additional limitation of existing DT-IMS devices is the low sensitivity of the Faraday Cup Electrometers at concentrations found in typical aerosols. Conversely, DT-IMS devices have the advantages of mobility invariant high resolving power (R~10-20), low drift gas flow rates compared to DMA sheath gas flowrates and shorter measurement times as compared to most scanning differential mobility analyzers.

The modifications to traditional DT-IMS devices that facilitated application for ambient aerosol measurement include a novel gateless sample introduction scheme, and the ability to couple to an aspirating Condensation Particle Counter (CPC), which can detect single particles. The gateless sample introduction, in embodiments, uses a combination of a controlled flow path and stepped voltage at the start of a measurement to effectively select a 'packet' of aerosol. Additional aerosol does not enter the sample region after the start of a measurement due to the presence of an electrostatic field. The coupling to a CPC, in embodiments, includes a controlled flow that splits to provide the drift gas and the gas aspirated by the CPC. A prototype device was built and has been tested. The device has a linear relationship between drift time and mobility and a resolving power greater than ~10. Measurements of proteins show good peak separation and compare well to DMA measurements.

Previous DT-IMS designs were unable to sample charged particles and require high ion concentrations. In contrast, the DT-IMS devices, systems and methods described herein allow for sampling of charged particles at relatively low concentrations.

In embodiments described herein, a sample inlet is provided where aerosol may be continuously introduced to the inlet. An electric field is applied at start of measurement, and packet of aerosol is selected. Drift gas removes stray particles from the drift region, and the field prevents additional aerosol from entering drift region. Inlet flow rate may be modified to adjust the length of aerosol packet. Shorter packets improve resolving power. Longer packets increase sensitivity.

In embodiments, described herein the end of the drift region is coupled to aspirating detector. Particle counts time is synced with the start of the application of the field. Drift gas is introduced with the aspirated supply flow. Vapors can be added to the drift gas to study vapor uptake by particles.

Figure 28:
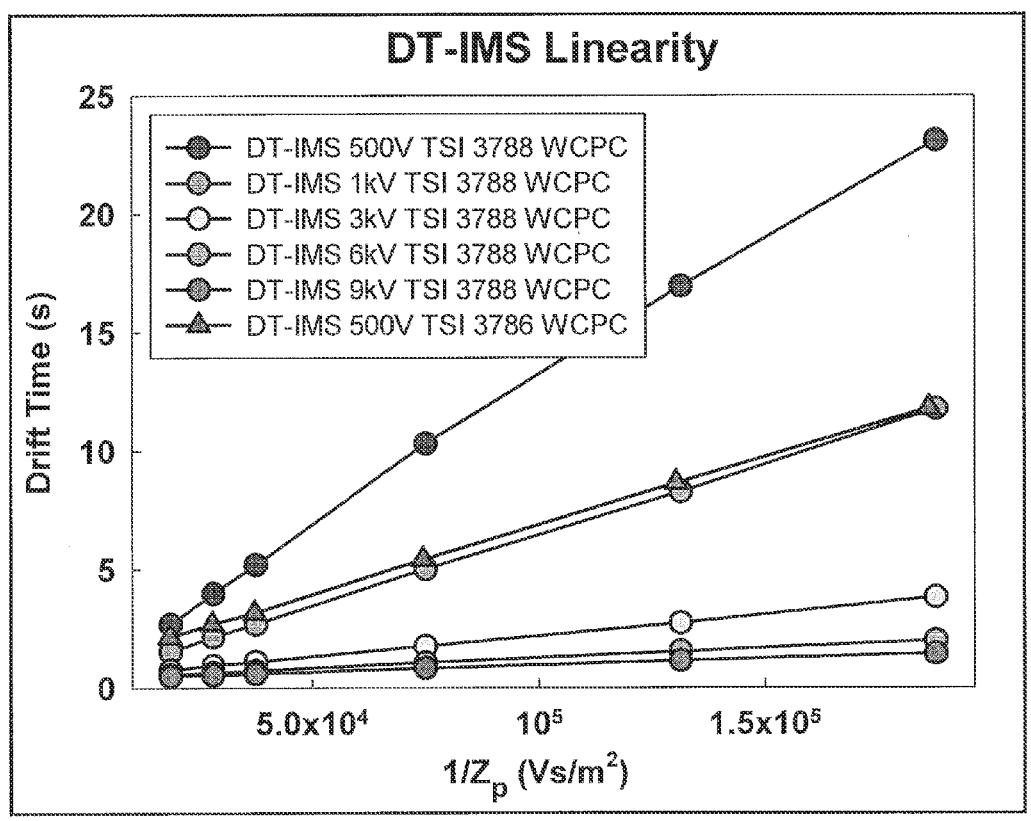
FIG. 28 is a plot of drift time at various voltages in a test DT-IMS system, showing linearity.

Using a system as shown in FIG. 16 and a DT-IMS as shown in FIG. 9, with the following operating parameters (inlet flow: 800 or 600 cm$^3$/min; drift flow: 200 cm$^3$/min; detector flow 600 cm$^3$/min), good linearity ($R^2$>0.998) for particles up to 6 nm for a wide range of drift voltages was observed. Calibration was dependent on detector. It was found that linearity suffers at long drift times. However, higher drift voltages show good linearity to 20 nm (see; e.g., FIG. 28).

With the prototype system used herein, it was found that DMA resolving power was the limiting factor for slow scans (low drift voltage), while the detector response time was the limiting factor for fast scans. The width of CPC detection time distribution was found to affect the resolving power, which was more apparent at faster scan times.

It was found that the transmission of particles varies with voltage and mobility, and that calibration may be used to correct. It was also found that higher drift voltages favor transmission of larger particles.

Thus, embodiments of DRIFT TUBE ION MOBILITY SPECTROMETER FOR AEROSOL MEASUREMENT are disclosed. One skilled in the art will appreciate that the articles, systems and methods described herein can be practiced with embodiments other than those disclosed. The disclosed embodiments are presented for purposes of illustration and not limitation.

What is claimed is:

1. A method comprising:
    introducing a sample aerosol into a drift tube of an ion mobility spectrometer;
    introducing a carrier gas into the drift tube of the ion mobility spectrometer such that at least a portion of the carrier gas flows through the drift tube in a direction generally opposing migration of ionized particles through the drift tube,
        wherein the sample aerosol and carrier gas are introduced into the drift tube such that the sample aerosol circulates within a portion of the drift tube, and
        wherein an applied electrostatic separation field blocks migration of ionized particles in the sample aerosol into a separation region of the drift tube; and
    applying a capturing electric field to the drift tube to increase the electrical potential of ionized particles within at least a portion of the sample circulation to a potential greater than that of the applied electrostatic separation field to allow the ionized particles at the increased potential to migrate in the drift tube down a gradient of the applied separation field against the flow of the carrier gas to separate according to their ion mobility.

2. A method according to claim 1, further comprising deactivating an electronic gate to allow at least a portion of the ionized particles having the increased potential to pass through the gate, wherein the gate is positioned within the drift tube electrically downstream of the sample circulation region.

3. A method according to claim 1, further comprising carrying the separated ionized particles via a stream of the carrier gas to a particle detector external to the drift tube.

4. A method according to claim 3, wherein the separated ionized particles are carried in a conduit, and wherein the drift tube, the conduit and flow of carrier gas is configured to cause a portion of the carrier gas to flow in the drift tube against the migration of the ionized particles down the gradient of the electric field and to cause a portion of the carrier gas to flow in the conduit.

5. A method according to claim 1, further comprising detecting the separated ionized particles via a particle detector, wherein the particle detector is a condensation particle counter.

6. A method according to claim 1, wherein applying the capturing electric field to the drift tube for purposes of ion mobility separation comprises applying the electric field such that a maximum voltage differential is achieved instantaneously or nearly instantaneously.

7. A method according to claim 1, wherein the electrostatic separation field is ramped or stepped over time.

8. A method according to claim 1, wherein introducing the sample aerosol into the drift tube of the ion mobility spectrometer comprises obtaining precursor aerosol and modifying the precursor aerosol to form the sample aerosol.

9. A method according to claim 8, wherein obtaining the precursor aerosol comprises selecting aerosol particles having a predetermined range of ion mobility.

10. A method according claim 9, wherein selecting the aerosol particles having the predetermined range of ion mobility comprises separating the particles via a differential mobility analyzer.

11. A method according to claim 8, wherein modifying the precursor aerosol comprises modifying the size, charge state, morphology or chemical composition of particles of the precursor aerosol to form the sample aerosol.

12. A method according to claim 1, wherein the carrier gas introduced into the drift tube comprises vaporized liquid.

13. A method comprising:
    introducing a sample aerosol into a drift tube of an ion mobility spectrometer;
    introducing a carrier gas into the drift tube of the ion mobility spectrometer such that at least a portion of the carrier gas flows through the drift tube in a direction generally opposing migration of ionized particles through the drift tube,
        wherein the sample aerosol and carrier gas are introduced into the drift tube such that the sample aerosol circulates within the drift tube in a manner such that (i) a portion of the sample aerosol circulation is within a region of the drift tube to which an electrostatic field is capable of being applied for purposes of ion mobility separation and (ii) a portion of the sample aerosol circulation is in a portion of the drift tube in which the electrostatic field, when applied, effectively blocks migration of additional ions into the separation region, applying an electric field to the drift tube for purposes of ion mobility separation, wherein the application of the electric field increases the electrical potential of ionized particles within the sample circulation in the region of the drift tube to which the electrostatic field is applied, wherein the ionized particles to which the electric field is applied migrate in the tube down a gradient of the applied field against the flow of the carrier gas to separate according to their ion mobility.

14. A method according to claim 13, further comprising deactivating an electronic gate to allow at least a portion of the ionized particles to which the electric field is applied to pass through the gate, wherein the gate is positioned within the drift tube electrically downstream of the sample circulation region.

15. A drift tube ion mobility spectrophotometer comprising:

a drift tube through which ionized particles are configured to drift against a flow of a carrier gas;

a detector positioned and configured to detect the ionized particles that have drifted through the drift tube against the flow of the carrier gas;

a first plurality of electrodes disposed about the drift tube and configured to apply an electrostatic field having a voltage gradient along a longitudinal axis of the drift tube, along which gradient the ionized particles drift against the flow of the carrier gas;

electronics operably coupled to the first plurality of electrodes and configured to control the electrostatic field applied via the electrodes;

a carrier gas inlet; and a sample inlet;

wherein the sample inlet, the drift tube, the electronics and the first plurality of electrodes are configured such that an aerosol introduced through the sample inlet circulates near a point in the drift tube where the voltage, in the direction of the longitudinal axis of the drift tube, is at zero when electrostatic field is applied via the first plurality of electrodes.

16. The DT-IMS of claim 15, further comprising a conduit configured to carry particles that migrate through the drift tube to the detector.

17. The DT-IMS of claim 16, wherein the carrier gas inlet, the conduit, and the drift tube are configured such that ionized particles that separate as they migrate towards the end of the drift tube are carried through the conduit by a stream of carrier gas, introduced through the carrier gas inlet.

18. The DT-IMS of claim 15, wherein the detector is a condensation particle counter.

19. The DT-IMS of claim 15, further comprising a second plurality of electrodes disposed about the drift tube and configured to increase the electrical potential of ionized particles at the point in the drift tube where the voltage, in the direction of the longitudinal axis of the drift tube, is at zero when electrostatic field is applied via the first plurality of electrodes, wherein the electronics are operably coupled to the second plurality of electrodes and are configured to control an electrostatic field applied via the second plurality of electrodes to increase the electrical potential of the ionized particles, and wherein one or more of the first plurality of electrodes are the same or different than one or more of the second plurality of electrodes.

20. The DT-IMS claim 19, further comprising an electronic gate positioned within the drift tube electrically downstream of the point in the drift tube where the voltage is at zero when electrostatic field is applied only via the first plurality of electrodes, wherein the electronic gate is operably coupled to the electronics.

21. A DT-IMS according to claim 15, wherein the first plurality of electrodes and the electronics are configured to apply the electrostatic field in a constant manner, non-constant manner, time invariant manner or time variant manner.

22. A DT-IMS of claim 21, wherein the first plurality of electrodes and the electronics are configured to apply the electrostatic field in a non-constant, increasing manner to focus ionized particles towards the longitudinal axis of the drift tube as the particles drift through the tube.

* * * * *